(12) United States Patent
Ryan et al.

(10) Patent No.: US 10,739,333 B2
(45) Date of Patent: *Aug. 11, 2020

(54) METHODS OF BH3 PROFILING

(71) Applicant: Dana-Farber Cancer Institute, Inc., Boston, MA (US)

(72) Inventors: Jeremy Ryan, Somerville, MA (US); Anthony Letai, Medfield, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/022,987

(22) PCT Filed: Sep. 18, 2014

(86) PCT No.: PCT/US2014/056284
§ 371 (c)(1),
(2) Date: Mar. 18, 2016

(87) PCT Pub. No.: WO2015/042249
PCT Pub. Date: Mar. 26, 2015

(65) Prior Publication Data
US 2016/0231314 A1    Aug. 11, 2016

Related U.S. Application Data

(60) Provisional application No. 61/879,869, filed on Sep. 19, 2013.

(51) Int. Cl.
*G01N 33/50* (2006.01)
*G01N 33/574* (2006.01)
*G01N 33/58* (2006.01)

(52) U.S. Cl.
CPC ..... *G01N 33/5079* (2013.01); *G01N 33/5011* (2013.01); *G01N 33/5035* (2013.01); *G01N 33/5748* (2013.01); *G01N 33/582* (2013.01); *G01N 2333/82* (2013.01); *G01N 2800/52* (2013.01)

(58) Field of Classification Search
CPC ........... G01N 33/5079; G01N 33/5011; G01N 33/5035; G01N 33/5748; G01N 33/582; G01N 33/5014; G01N 33/5023; G01N 33/5032; G01N 33/5094; G01N 2800/52
See application file for complete search history.

(56) References Cited

U.S. PATENT DOCUMENTS

| | | |
|---|---|---|
| 4,522,811 A | 6/1985 | Eppstein et al. |
| 4,676,980 A | 6/1987 | Segal et al. |
| 4,816,567 A | 3/1989 | Cabilly et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,674,980 A | 10/1997 | Frankel et al. |
| 5,804,604 A | 9/1998 | Frankel et al. |
| 5,916,771 A | 6/1999 | Hori et al. |
| 5,939,598 A | 8/1999 | Kucherlapati et al. |
| 5,965,703 A | 10/1999 | Horne et al. |
| 7,064,193 B1 | 6/2006 | Cory et al. |
| 7,714,005 B2 | 5/2010 | Chen et al. |
| 7,868,133 B2 | 1/2011 | Korsmeyer et al. |
| 8,221,966 B2 | 7/2012 | Letai |
| 9,360,473 B2 | 6/2016 | Cardone |
| 9,540,674 B2 * | 1/2017 | Letai .................. G01N 33/5011 |
| 9,856,303 B2 | 1/2018 | Korsmeyer et al. |
| 9,902,759 B2 | 2/2018 | Korsmeyer et al. |
| 10,393,733 B2 | 8/2019 | Letai et al. |
| 2002/0115613 A1 | 8/2002 | Kumar |
| 2004/0171809 A1 | 9/2004 | Korsmeyer et al. |
| 2007/0027175 A1* | 2/2007 | Shaughnessy, Jr. ......................... A61K 31/4745 514/283 |
| 2008/0199890 A1 | 8/2008 | Letai |
| 2008/0234201 A1 | 9/2008 | Korsmeyer et al. |
| 2010/0286057 A1 | 11/2010 | Walensky et al. |
| 2011/0130309 A1 | 6/2011 | Cardone |
| 2011/0154522 A1 | 6/2011 | Korsmeyer et al. |
| 2013/0122492 A1 | 5/2013 | Khosravi et al. |
| 2013/0149718 A1 | 6/2013 | Letai |

(Continued)

FOREIGN PATENT DOCUMENTS

| | | |
|---|---|---|
| JP | 2009-532033 A | 9/2009 |
| JP | 2009-542195 A | 12/2009 |

(Continued)

OTHER PUBLICATIONS

Ryan et al. Heightened mitochondrial priming is the basis for apoptotic hypersensitivity of CD4+ CD8+ thymocytes. PNAS 107 (29): 12895-12900 (Jul. 20, 2010).*

(Continued)

*Primary Examiner* — Gailene Gabel
(74) *Attorney, Agent, or Firm* — Wolf, Greenfield & Sacks, P.C.

(57) ABSTRACT

In various aspects the invention provides methods of predicting sensitivity of a cancer cell to a therapeutic agent by contacting a test cell population BH3 domain peptide; measuring the amount of BH3 domain peptide induced mitochondrial outer membrane permeabilization in the test cell population; and comparing the amount of BH3 domain peptide induced mitochondrial outer membrane permeabilization in the test cell population to a control cell population that has not been contacted with the therapeutic agent. An increase in mitochondrial membrane permeabilization in the test cell population compared to the control cell population indicates the cell is sensitive to the therapeutic agent.

20 Claims, 7 Drawing Sheets
Specification includes a Sequence Listing.

(56) References Cited

U.S. PATENT DOCUMENTS

| | | | |
|---|---|---|---|
| 2015/0362479 A1* | 12/2015 | Letai | G01N 33/5011 435/29 |
| 2016/0200786 A1 | 7/2016 | Korsmeyer et al. | |
| 2016/0258933 A1 | 9/2016 | Letai | |
| 2017/0160267 A9 | 6/2017 | Letai | |
| 2017/0184567 A1 | 6/2017 | Letai | |
| 2018/0120297 A1 | 5/2018 | Letai et al. | |
| 2018/0128813 A1 | 5/2018 | Letai et al. | |
| 2018/0244740 A1 | 8/2018 | Korsmeyer et al. | |

FOREIGN PATENT DOCUMENTS

| | | |
|---|---|---|
| WO | WO 91/00360 A1 | 1/1991 |
| WO | WO 92/20373 A1 | 11/1992 |
| WO | WO 93/08829 A1 | 5/1993 |
| WO | WO 94/02602 A1 | 2/1994 |
| WO | WO 94/11026 A2 | 5/1994 |
| WO | WO 96/27011 A1 | 9/1996 |
| WO | WO 96/33735 A1 | 10/1996 |
| WO | WO 96/34096 A1 | 10/1996 |
| WO | WO 97/05265 A1 | 2/1997 |
| WO | WO 99/53049 A1 | 10/1999 |
| WO | WO 00/59526 A1 | 10/2000 |
| WO | WO 01/12661 A2 | 2/2001 |
| WO | WO 02/20568 A2 | 3/2002 |
| WO | WO 03/040168 A2 | 5/2003 |
| WO | WO 2004/022580 A2 | 3/2004 |
| WO | WO 2004/058804 A1 | 7/2004 |
| WO | WO 2005/044839 A2 | 5/2005 |
| WO | WO 2006/099667 A1 | 9/2006 |
| WO | WO 2007/123791 A2 | 11/2007 |
| WO | WO 2007/149270 A2 | 12/2007 |
| WO | WO 2008/021484 A2 | 2/2008 |
| WO | WO 2010/147961 A1 | 12/2010 |
| WO | WO 2013/170176 A2 | 11/2013 |
| WO | WO 2013/188978 A1 | 12/2013 |
| WO | WO 2014/047342 A1 | 3/2014 |
| WO | WO 2015/010094 A1 | 1/2015 |
| WO | WO 2015/042249 A1 | 3/2015 |
| WO | WO 2016/176288 A1 | 11/2016 |
| WO | WO 2016/176299 A1 | 11/2016 |

OTHER PUBLICATIONS

Soltow et al. Overexpression of CuZnSOD or MnSOD protects satellite cells from doxorubicin-induced apoptosis. FASEB J 21: A449 (Apr. 2007) Abstract.*

Quinsay et al. Proapoptotic Bnip3 Mediates Permeabilization of Mitochondria and Release of Cytocrome c via a Novel Mechanism. Circulation 118 (18): Supply 2, S388 (Oct. 28, 2008) Abstract.*

Campos et al. Method for Monitoring pf Mitochondrial Cytochrome c Release During Cell Death: Immunodetection of Cytochrome c by Flow Cytometry After Selective Permeabilization of the Plasma Membrane. Cytometry Part A 69A: 515-523 (2006).*

U.S. Appl. No. 10/658,028, filed Sep. 9, 2003, Abandoned, 2004-0171809.

U.S. Appl. No. 11/789,557, filed Apr. 24, 2007, Granted, U.S. Pat. No. 7,868,133.

U.S. Appl. No. 12/966,821, filed Dec. 13, 2010, Published, 2011-0154522.

U.S. Appl. No. 15/073,356, filed Mar. 17, 2016, Pending.

U.S. Appl. No. 11/695,321, filed Apr. 2, 2007, Granted, U.S. Pat. No. 8,221,966.

U.S. Appl. No. 13/478,831, filed May 23, 2012, Published, 2013-0149718.

U.S. Appl. No. 15/073,391, filed Mar. 17, 2016, Pending.

U.S. Appl. No. 14/429,272, filed Mar. 18, 2015, Published, 2015-0362479.

EP03749602.3, Jun. 7, 2006, Supplementary Partial European Search Report.

EP03749602.3, Sep. 28, 2006, Supplementary Partial European Search Report.

PCT/US2003/028482, Dec. 8, 2005, International Search Report.

PCT/US2007/008055, Jan. 2, 2008, International Search Report and Written Opinion.

PCT/US2007/008055, Sep. 30, 2008, International Preliminary Report on Patentability.

PCT/US2013/060707, Jan. 9, 2014, International Search Report and Written Opinion.

PCT/US2013/060707, Apr. 2, 2015, International Preliminary Report on Patentability.

PCT/US2014/056284, Dec. 31, 2014, International Search Report and Written Opinion.

PCT/US2014/056284, Mar. 31, 2016, International Preliminary Report on Patentability.

Extended European Search Report for EP14845952.2 dated Mar. 27, 2017.

International Search Report and Written Opinion for PCT/US2016/029495 dated Aug. 5, 2016.

International Preliminary Report on Patentability for PCT/US2016/029495 dated Nov. 9, 2017.

International Search Report and Written Opinion for PCT/US2016/029510 dated Aug. 12, 2016.

International Preliminary Report on Patentability for PCT/US2016/029510 dated Nov. 9, 2017.

Barretina et al., The Cancer Cell Line Encyclopedia enables predictive modelling of anticancer drug sensitivity. Nature. Mar. 29, 2012;483(7391):603-7. doi: 10.1038/nature11003. Erratum in: Nature Dec. 13, 2012;492(7428):290.

Buron et al., Use of human cancer cell lines mitochondria to explore the mechanisms of BH3 peptides and ABT-737-induced mitochondrial membrane permeabilization. PLoS One Mar. 31, 2010;5(3):e9924. doi:10.1371/journal.pone.0009924.

Friedman et al., Precision medicine for cancer with next-generation functional diagnostics. Nat Rev Cancer Dec. 2015;15(12):747-56. doi: 10.1038/nrc4015. Epub Nov. 5, 2015.

Letai, Perturbing cancer cell mitochondria to learn how to kill cancer with BH3 profiling. Broad Institute, Seminar Series on Cell Circuits and Epigenomics Jul. 28, 2014 Presentation.

Long et al., Optimization and validation of mitochondria-based functional assay as a useful tool to identify BH3-like molecules selectively targeting anti-apoptotic Bcl-2 proteins. BMC Biotechnol. May 24, 2013;13:45. doi: 10.1186/1472-6750-13-45.

Oliver et al., Permeabilization of Cell Membranes. C. Oliver and M.C. Jamur (eds.), Immunocytochemical Methods and Protocols, Methods in Molecular Biology, vol. 588, DOI 10.1007/978-1-59745-324-0_9, © Humana Press, a part of Springer Science + Business Media, LLC 1995, 1999, 2010. Chapter 9: 4 pages.

Ryan et al., BH3 profiling in whole cells by fluorimeter or FACS. Methods. Jun. 1, 2013;61(2):156-64. doi: 10.1016/j.ymeth.2013.04.006. Epub Apr. 20, 2013.

Sen et al., Artemisinin triggers induction of cell-cycle arrest and apoptosis in Leishmania donovani promastigotes. J Med Microbiol. Sep. 2007;56(Pt 9):1213-8.

Song et al., Carbon monoxide promotes Fas/CD95-induced apoptosis in Jurkat cells. J Biol Chem. Oct. 22, 2004;279(43):44327-34. Epub Jul. 27, 2004. Erratum in: J Biol Chem. Jun. 10, 2005;280(23):22555.

Sugiyama et al., Activation of mitochondrial voltage-dependent anion channel by a pro-apoptotic BH3-only protein Bim. Oncogene Jul. 25, 2002;21(32):4944-56.

Vaquero et al., Extracellular matrix proteins protect pancreatic cancer cells from death via mitochondrial and nonmitochondrial pathways. Gastroenterology Oct. 2003;125(4):1188-202.

Campos et al., Method for monitoring of mitochondrial cytochrome c release during cell death: Immunodetection of cytochrome c by flow cytometry after selective permeabilization of the plasma membrane. Cytometry Part A. Jun. 2006;69(6):515-23.

Extended European Search Report for EP16787039.3 dated Oct. 4, 2018.

Extended European Search Report for EP16787045.0 dated Oct. 4, 2018.

(56) References Cited

OTHER PUBLICATIONS

Akgul et al., In vivo localisation and stability of human Mcl-1 using green fluorescent protein (GFP) fusion proteins. FEBS Lett. Jul. 28, 2000;478(1-2):72-6.
Emerman et al., Effects of defined medium, fetal bovine serum, and human serum on growth and chemosensitivities of human breast cancer cells in primary culture: inference for in vitro assays. In Vitro Cell Dev Biol. Feb. 1987;23(2):134-40.
Rizvi et al., Platelet-derived growth factor primes cancer-associated fibroblasts for apoptosis. J Biol Chem. Aug. 15, 2014;289(33):22835-49. doi:10.1074/jbc.M114.563064. Epub Jun. 27, 2014.
Supplementary Partial European Search Report for EP03749602.3 dated Jun. 7, 2006.
Supplementary Partial European Search Report for EP03749602.3 dated Sep. 28, 2006.
International Search Report for PCT/US2003/028482 dated Dec. 8, 2005.
International Search Report and Written Opinion for PCT/US2007/008055 dated Jan. 2, 2008.
International Preliminary Report on Patentability for PCT/U2007/008055 dated Sep. 30, 2008.
International Search Report and Written Opinion for PCT/US2013/060707 dated Jan. 9, 2014.
International Preliminary Report on Patentability for PCT/US2013/060707 dated Apr. 2, 2015.
International Search Report and Written Opinion for PCT/US2014/056284 dated Dec. 31, 2014.
International Preliminary Report on Patentability for PCT/US2014/056284 dated Mar. 31, 2016.
Adams, et al., The Bcl-2 Protein Family: Arbiters of Cell Survival. Science. 1998;281(5381):1322-1326.
Ait-Ikhlef et al. The motoneuron degeneration in the wobbler mouse is independent of the overexpression of a Bcl2 transgene in neurons. Neurosci. Lett. 1995;199:163-6.
Bae et al., Underphosphorylated BAD interacts with diverse antiapoptotic Bcl-2 family proteins to regulate apoptosis. Apoptosis. 2001;6:319-30.
Bouillet et al., Proapoptotic Bcl-2 Relative Bim Required for Certain Apoptotic Responses, Leukocyte Homeostatis, and to Preclude Autoimmunity. Science. 1999;286:1735-8.
Boyd et al., Bik, a novel death-inducing protein shares a distinct sequence motif with Bcl-2 family proteins and interacts with viral and cellular survival-promoting proteins. Oncogene. 1995;11:1921-8.
Brady et al., Reflections on a peptide. Nature. 1994;368:692-3.
Brennan et al., Preparation of Bispecific Antibodies by Chemical Recombination of Monoclonal Immunoglobulin $G_1$ Fragments. Science. 1985;229:81.
Calin et al., A MicroRNA Signature Associated with Prognosis and Progression in Chronic Lymphocytic Leukemia. N. Engl. J. Med. 2005;353:1793-801.
Caron et al., Engineered Humanized Dimeric Forms of IgG Are More Effective Antibiotics. J. Exp. Med. 1992;176:1191-5.
Cartron et al., The first α Helix of Bax Play a Necessary Role in Its Ligand-Induced Activation by the BH3-Only Proteins Bid and PUMA. Mol. Cell 2004;16:807-18.
Certo et al., Mitochondria Primed by Death Signals Determine Cellular Addiction to Antiapoptotic BCL-2 Family Members. Cancer Cell. May 2006;9:351-65.
Chen et al., Caspase cleavage of $Bim_{EL}$ triggers a positive feedback amplification of apoptotic signaling. Proc. Natl. Acad. Sci. USA. 2004;101(5):1235-40.
Chen et al., Differential Targeting of Prosurvival Bcl-2 Proteins by Their BH3-Only Ligands Allows Complementary Apoptotic Function. Mol. Cell. 2005;17:393-403.
Cheng et al., Bax-independent inhibition of apoptosis by $Bcl-X_L$. Nature. 1996;379:554-6.
Cheng et al., BCL-2, $BCL-X_L$ Sequester BH3 Domain-Only Molecules Preventing BAX- and BAK-Mediated Mitochondrial Apoptosis. Mol. Cell. 2001;8:705-11.
Chipuk et al., Direct Activation of Bax by p53 Mediates Mitochondrial Membrane Permeabilization and Apoptosis. Science. 2004;303:1010-4.
Chittenden et al., A conserved domain in Bak, distinct form BH1 and BH2, mediates cell death and protein binding functions. EMBO J. 1995;14(22):5589-96.
Chittenden et al., Induction of apoptosis by the Bcl-2 homologue Bak. Nature. 1995;374(6524):733-6.
Chonghaile et al., Pretreatment mitochondrial priming correlates with clinical response to cytotoxic chemotherapy. Science. Nov. 25, 2011;334(6059):1129-33. doi: 10.1126/science.1206727. Epub Oct. 27, 2011.
Cole et al., The EBV-Hybridoma technique and its application to human lung cancer. Monoclonal Antibodies and Cancer Therapy. 1985:77-96.
Cory et al., The Bcl2 Family: Regulators of the Cellular Life-Or-Death Switch. Nat. Rev. Cancer. 2002;2(9):647-56.
Cosulich et al., Regulation of apoptosis by BH3 domains in a cell-free system. Curr. Biol. 1997;7(12):913-20.
Cote et al., Generation of human monoclonal antibiotics reactive with cellular antigens. Proc. Natl. Acad. Sci. USA. 1983;80:2026-30.
Czabotar et al., Bax Activation by Bim? Cell Death and Differentiation. Sep. 2009;16:1187-91.
Davids et al., BH3 profiling demonstrates that restoration of apoptotic priming contributes to increased sensitivity to PI3K inhibition in stroma-exposed chronic lymphocytic leukemia cells. Blood 118(21). Nov. 18, 2011. Abstract.
Davids et al., Targeting the B-cell lymphoma/leukemia 2 family in cancer. J Clin Oncol. Sep. 1, 2012;30(25):3127-35. doi: 10.1200/JCO.2011.37.0981. Epub May 29, 2012.
Degrado, Designs of peptides and proteins. Adv Protein Chem. 1988;39:51-124.
Deng et al., BH3 Profiling Identifies Three Distinct Classes of Apoptotic Blocks to Predict Response to ABT-737 and Conventional Chemotherapeutic Agents. Cancer Cell. Aug. 2007;12:171-85.
Derenne et al., Antisense strategy shows that Mcl-1 rather than Bcl-2 or Bcl-xL is an essential survival protein of human myeloma cells. Blood. 2002;100:194-9.
Desagher et al., Bid-induced Conformational Change of Bax Is Responsible for Mitochondrial Cytochrome c Release during Apoptosis. J. Cell Biol. 1999;144(5):891-901.
Di Lisa et al., Mitochondrial Function and Cell Injury in Single Cardiac Myocytes Exposed to Anoxia and Reoxygenation. Transplant Proc. 1995;27(5):2829-30.
Di Lisa et al., Mitochondrial membrane potential in single living adult rat cardiac myocytes exposed to anoxia or metabolic inhibition. J. Physiol. 1995;486(1):1-13.
Dohner et al., Genomic Aberrations and Survival in Chronic Lymphocytic Leukemia. N. Engl. J. Med. 2000;343:1910-16.
Egle et al., Bim is a suppressor of Myc-induced mouse B cell leukemia. Proc. Natl. Acad. Sci. USA. 2004;101(16):6164-9.
Ellerby, et al., Anti-cancer activity of targeted pro-apoptotic peptides. Nat. Med. 1999;5(9):1032-8.
Elliott et al., Intercellular Trafficking and Protein Delivery by a Herpesvirus Structural Protein. Cell. 1997;88:223-33.
Eskes et al., Bid Induces the Oligomerization and Insertion of Bax into the Outer Mitochondrial Membrane. Mol. Cell. Biol. 2000;20(3):929-35.
Fanidi et al., Cooperative interaction between c-myc and -2 proto-oncogenes. Nature. 1992;359:554-6.
Fishwild et al., High-avidity human IgGk monoclonal antibodies from a novel strain of minilocus transgenic mice. Nature Biotechnology. 1996;14:845-51.
Frankel et al., Activity of synthetic peptides from the Tat protein of human immunodeficiency virus type 1. Proc. Natl. Acad. Sci. USA. 1989;86:7397-401.
Fuchs et al., Pathway for Polyarginine Entry into Mammalian Cells. Biochemistry Mar. 2004;43(9):2438-44.
Futaki et al., Arginine-rich Peptides: An Abundant Source of Membrane-Permeable Peptides Having Potential as Carriers for Intracellular Protein Delivery. J. Biol. Chem. 2001;276(8):5836-40.

(56) References Cited

OTHER PUBLICATIONS

Green et al., A matter of life and death. Cancer Cell. 2002;1:19-30.
Green et al., The Pathophysiology of Mitochondrial Cell Death. Science. 2004;305:626-9.
Green, Life, Death, BH3 Profiles, and the Salmon Mousse. Cancer Cell. Aug. 2007;12:97-9.
Griffiths et al., Cell Damage-induced Conformational Changes of the Pro-Apoptotic Protein Bak In Vivo Precede the Onset of Apoptosis. J. Cell Biol. 1999;144(5):903-14.
Gross et al., Enforced dimerization of BAX results in its translocation, mitochondrial dysfunction and apoptosis. EMBO J. 1998;17(14):3878-85.
Grosschedl et al., Introduction of μ immunoglobulin gene into the mouse germ line: specific expression in lymphoid cells and synthesis of functional antibody. Cell. 1984;38:647-58.
Gruber et al., Efficient Tumor Cell Lysis Mediated by a Bispecific Single Chain Antibody Expressed in *Escherichia coli*. J. Immunol. 1994;152:5368-74.
Gul et al., Apoptotic blocks and chemotherapy resistance: strategies to identify Bcl-2 protein signatures. Briefings in Functional Genomics and Proteomics. Jan. 2008;7(1):27-34.
Hanahan et al., Heritable formation of pancreatic β-cell tumors in transgenic mice expressing recombinant insulin/simian virus 40 oncogenes. Nature. 1985;315:115-22.
Hanahan et al., The Hallmarks of Cancer. Cell. 2000;100:57-70.
Hans et al., Beta-carbolines induce apoptosis in cultured cerebellar granule neurons via the mitochondrial pathway. Neuropharmacology. Jan. 2005;48(1):105-17.
Harada et al., Survival factor-induced extracellular signal-regulated kinase phosphorylates BIM, inhibiting its association with BAX and proapoptotic activity. Proc. Natl. Acad. Sci. USA. 2004;101(43):15313-7.
Hemann et al., Evasion of the p53 tumour surveillance network by tumour-derived MYC mutants. Nature. 2005;436:807-11.
Hemann et al., Suppression of tumorigenesis by the p53 target PUMA. Proc. Natl. Acad. Sci. USA. 2004;101(25):9333-8.
Hengartner et al., C. elegans Cell Survival Gene ced-9 Encodes a functional Homolog of the Mammalian Proto-Oncogene bcl-2. Cell. 1994;76:665-76.
Holinger et al., Bak BH3 Peptides Antagonize Bcl-x.sub.L Function and Induce Apoptosis through Cytochrome c-independent Activation of Caspases. J. Biol. Chem. 1999;274(19):13298-304.
Holliger et al., Diabodies: Small bivalent and bispecific antibody fragments. Proc. Natl. Acad. Sci. USA. 1993;90:6444-8.
Hoogenboom et al., By-passing Immunisation, Human Antibodies from Synthetic Repertoires of Germline VH Gene segments rearranged in Vitro. J. Mol. Biol. 1992;227:381-8.
Hopp et al., Prediction of protein antigenic determinants from amino acid sequences. Proc. Natl. Acad. Sci. USA. 1981;78:3824-8.
Hsu et al., Nonionic Detergents Induce Dimerization among Members of the Bcl-2 Family. J. Biol. Chem. 1997;272(21):13829-34.
Huang et al., BH3-Only Proteins—Essential Initiators of Apoptotic Cell Death. Cell. 2000;103:839-42.
Huse et al., Generation of a large Combinatorial Library of the Immunoglobulin Repertoire in Phage Lambda. Science. 1989;246:1275-81.
Inohara et al., Harakiri, a novel regulator of cell death, encodes a protein that activates apoptosis and interacts selectively with survival-promoting proteins Bcl-2 and Bcl-$X_L$. Embo J. 1997;16(7):1686-94.
Jackson et al., Heat shock induces the release of fibroblast growth factor 1 from NIH 3T3 cells. Proc. Natl. Acad. Sci. USA. 1992;89:10691-5.
Jameson et al., A rationally designed CD4 analogue inhibits experimental allergic encephalomyelitis. Nature. 1994;368:744-6.
Jones et al., Nature, Replacing the complementarily-determining regions in a human antibody with those from a mouse. 1986;321:522-5.
Jonkers et al., Oncogene addiction: Sometimes a temporary slavery. Cancer Cell. 2004;6:535-8.

Kelekar et al., Bad is a BH3 Domain-Containing Protein that Forms an Inactivating Dimer with Bcl-$X_L$. Mol. Cell Biol. 1997;17(12):7040-6.
Kelekar et al., Bcl-2-family proteins: the role of the BH3 domain in apoptosis. Trends Cell Biol. 1998;8:324-30.
Kohler et al., Continuous cultures of fused cells secreting anti-body of predefined specificity. Nature. 1975;256:495-7.
Korsmeyer et al., Pro-apoptotic cascade activates BID, which oligomerizes BAK or BAX into pores that result in the release of cytochrome c. Cell Death Differ. Dec. 2000;7(12):1166-73.
Kostelny et al., Formation of a Bispecific antibody by the Leucine Zippers. J. Immunol. 1992;148(5):1547-53.
Kozbor et al., The production of monoclonal antibodies from human lymphocytes. Immunol Today. 1983;4:72-9.
Kozbor, A human hybrid Myeloma for production of human monoclonal antibodies. J. Immunol. 1984;133:3001-5.
Krieg, Mechanisms and applications of immune stimulatory CpG oligodeoxynucleotides. Biochim Biophys Acta. 1999;1489(1):107-16.
Kuwana et al., BH3 Domains of BH3-Only Proteins Differentially Regulate Bax-Mediated Mitochondrial Membrane Permeabilization Both Directly and Indirectly. Mol. Cell. 2005;17:525-35.
Kuwana et al., Bid, Bax, and Lipids Cooperate to Form Supramolecular Openings in the Outer Mitochondrial Membrane. Cell. 2002;111:331-42.
Kyte et al., A Simple Method for displaying the Hydropathic Character of a protein. J. Mol. Biol. 1982;157:105-42.
La Vieira, et al., Cell permeable BH3-peptides overcome the cytoprotective effect of Bcl-2 and Bcl-$X_L$. Oncogene. 2002;21(13):1963-77.
Leo et al., Characterization of the Antiapoptotic Bcl-2 Family Member Myeloid Cell Leukemia-1 (Mcl-1) and the Stimulation of Its Message by Gonadotropins in the Rat Ovary. Endocrinol. 1999;140(12):5469-77.
Letai et al., Antiapoptotic BcL-2 is required for maintenance of a model leukemia. Cancer Cell. 2004;6:241-9.
Letai et al., Distinct BH3 domains either sensitize or activate mitochondrial apoptosis, serving as prototype cancer therapeutics. Cancer Cell. Sep. 2002;2(3):183-92.
Letai, The BCL-2 network: Mechanistic insights and therapeutic potential. Drug Disc.Today: Disease Mechanisms. 2005;2(2):145-51.
Letai, BH3 domains as BCL-2 inhibitors: prototype cancer therapeutics. Expert Opin Biol Ther. Apr. 2003;3(2):293-304.
Li et al., tsg 101: A novel tumor susceptibility gene isolated by controlled Homozygous functional knockout of Allelic Loci in Mammalian Cells. Cell. 1996;85:319-29.
Li et al., Cleavage of BID by Caspase 8 Mediates the Mitochondrial Damage in the Fas Pathway of Apoptosis. Cell. 1998;94(4):491-501.
Li et al., Endonuclease G is an apoptotic DNase when released from mitochondria. Nature. 2001;412:95-9.
Liu et al., Bax conformational change is a crucial step for PUMA-mediated apoptosis in human leukemia. Biochem Biophys Res Commun. 2003;310(3):956-62.
Lonberg et al., Antigen-specific human antibodies from mice comprising four distinct genetic modifications. Nature. 1994;368:856-9.
Lonberg et al., Human Antibodies from Transgenic Mice. Intern Rev Immunol. 1995;13:65-93.
Luo et al., Bid, a Bcl2 interacting protein, mediates cytochrome c release from mitochondria in response to activation of cell surface death receptors, Cell. 1998;94(4):481-90.
Lutter et al., The pro-apoptotic Bcl-2 family member tBid localizes to mitochondrial contact sites. BMC Cell Biology. 2001;2:22.
Marani et al., Identification of Novel Isoforms of the BH3 Domain Protein Bim which Directly Activate Bax to Trigger Apoptosis. Mol Cell Biol. 2002;22(11):3577-89.
Marks et al., By-passing Immunization human Antibodies from v-gene libraries displayed on phage. J. Mol. Biol. 1991;222:581.
Marks et al., By-passing immunization: building high affinity human antibodies by chin shuffling. Bio/Technology. 1992;10:779-83.
Martin, Opening the Cellular Poison Cabinet. Science. Dec. 2010;330:1330-1.

(56) References Cited

OTHER PUBLICATIONS

Mason et al., The Hypogonadal mouse: reproductive functions restored by gene therapy. Science. 1986;234:1372-8.
Matsushita et al., A high-efficiency protein transduction system demonstrating the role of PKA in long-lasting long-term potentiation. J. Neuroscience. 2001;21(16):6000-7.
Matsuzaki, Why and how are peptide-lipid interactions utilized for self-defense? Biochem. Soc. Transactions. 2001;29:598-601.
McDonnell et al., bcl-2-Immunoglobulin Transgenic Mice Demonstrate Extended B Cell Survival and Follicular Lymphoproliferation. Cell. 1989;57:79-88.
Means et al., Modifications to change properties in Chemical Modification of Protein. 1974. Chapter 3, pp. 35-54, Holden-Day.
Milstein et al., Hybrid hybridomas and their use in immunohistochemistry. Nature. 1983;305:537-9.
Montero et al., Drug-induced death signaling strategy rapidly predicts cancer response to chemotherapy. Cell. Feb. 26, 2015;160(5):977-90. doi:10.1016/j.cell.2015.01.042.
Morrison et al., Success in specification. Nature. 1994;368:812-3.
Muchmore et al., X-ray and NMR structure of human Bcl-x.sub.L, an inhibitor of programmed cell death. Nature. 1996;381:335-41.
Munson et al., LIGAND: A Versatile Computerized Approach for Characterization of Ligand-Binding Systems. Analytical Biochemistry. 1980;107:220-39.
Nakano et al., PUMA, a Novel Proapoptotic Gene, is Induced by p53. Mol. Cell. 2001;7:683-94.
Narita, et al., bax interacts with the permeability transition pore to induce permeability transition and cytochrome c release in isolated mitochondria. Proc. Natl. Acad. Sci. USA. 1998;95:14681-6.
Neuberger et al., Generating high-avidity human Mabs in mice. Nature Biotechnology. 1996;14:826.
O'Brien et al., Phase I and II Multicenter Study of Oblimersen Sodium, a Bcl-2 Antisense Oligonucleotide, in Patients With Advanced Chronic Lymphocytic Leukemia. J. Clin. Oncol. 2005;23(30):7697-702.
O'Connor et al., Bim: a novel member of the Bcl-2 family that promotes apoptosis. Embo J. 1998;17(2):384-95.
Oda et al., Noxa, a BH3-Only Member of the Bcl-2 Family and Candidate Mediator of p53-Induced Apoptosis. Science. 2000;288:1053-8.
Oh et al., Conformational Changes in BID, a Pro-apoptotic BCL-2 Family Member, upon Membrane Binding. J. Biol. Chem. 2005;280(1):753-67.
Oltersdorf et al., An inhibitor of Bcl-2 family proteins induces regression of solid tumours. Nature. 2005;435:677-81.
Opferman et al., Development and maintenance of B and T lymphocytes requires antiapoptotic MCL-1. Nature. 2003;426:671-6.
Pinkert et al., An albumin enhancer located 10 kb upstream functions along with its promoter to direct efficient, liver-specific expression in transgenic mice. Genes and Dev. 1987;1:268-276.
Polster et al., BH3 Death Domain Peptide Induces Cell Type-selective Mitochondrial Outer Membrane Permeability. J. Biol. Chem. 2001;276 (41):37887-94.
Presta, Antibody engineering. Curr. Op. Struct. Biol. 1992;2:593-6.
Putcha et al., Induction of BIM, a Proapoptotic Bh3-Only BCL-2 Family Member, Is Critical for Neuronal Apoptosis. Neuron. 2001;29(3):615-28.
Puthalakath et al., Bmf: a Proapoptotic BH3-Only Protein Regulated by Interaction with the Myosin V Actin Motor Complex, Activated by Anoikis. Science. 2001;293:1829-32.
Puthalakath et al., Keeping killers on a tight leash: transcriptional and post-translational control of the pro-apoptotic activity of BH3-only proteins. Cell Death Differ. 2002;9:505-12.
Puthalakath et al., The Proapoptotic Activity of the Bcl-2 Family Member Bim is Regulated by Interaction with the Dynein Motor Complex. Mol. Cell. 1999;3:287-96.
Raff, Social controls on cell survival and cell death. Nature. 1992;356:397-400.

Rassenti et al., ZAP-70 Compared with Immunoglobulin Heavy-Chain Gene Mutation Status as a predictor of Disease Progression in Chronic Lymphocytic Leukemia. N. Engl. J. Med. 2004;351:893-901.
Ray et al., BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites. J. Biol. Chem. 2000;275(2):1439-48.
Readhead et al., Expression of a myelin basic protein gene in transgenic shiverer mice: correction of the dysmyelinating phenotype. Cell. 1987;48:703-12.
Ren et al., BID, BIM, and PUMA Are Essential for Activation of the BAX- and BAK-Dependent Cell Death Program. Science. Dec. 2010;330:1390-3.
Riechmann et al., Reshaping human antibodies for therapy. Nature. 1988;332:323-7.
Rothbard et al., Conjugation of arginine oligomers to cyclosporine A facilitates topical delivery and inhibition of inflammation. Nature Med. 2000;6(11):1253-7.
Ryan et al., Heightened mitochondrial priming is the basis for apoptotic hypersensitivity of CD4+ CD8+ thymocytes. Proc Natl Acad Sci U S A. Jul. 20, 2010;107(29):12895-900. doi: 10.1073/pnas.0914878107. Epub Jul. 6, 2010.
Samson et al., A 35 amino acid fragment of leptin inhibits feeding in the rat. Endocrinology. 1996;137:5182-5.
Sattler et al., Structure of Bcl-x.sub.L-Bak Peptide Complex: Recognition Between Regulators of Apoptosis. Science. 1997;275:983-6.
Schimmer et al., Cell Death and Differentiation. 2001;8(7):725-33. Sequence Search Result.
Shalaby et al., Development of humanized bispecific antibodies reactive with cytotoxic lymphocytes and tumor cells overexpressing the HER2 protooncogene. Exp. Med. 1992;175:217-25.
Shangary et al., Peptides derived from BH3 domains of Bcl-2 family members: a comparative analysis of inhibition of Bcl-2, Bcl-x(L) and Bax oligomerization, induction of cytochrome c release, and activation of cell death. Biochemistry. Jul. 30, 2002;41(30):9485-95.
Shimizu et al., Proapoptotic BH3-only Bcl-2 family members induce cytochrome c release, but not mitochondrial membrane potential loss, and do not directly modulate voltage-dependent anion channel activity. Proc Natl Acad Sci U S A. Jan. 18, 2000;97(2):577-82.
Shopes, A genetically engineered human IgG mutant with enhanced cytolytic activity. J Immunol. 1992. 148:2918-2922.
Stevenson et al., A chimeric antibody with dual Fc regions (bisFabFc) prepared by manipulations at the IgG hinge. Anti-Cancer Drug Design. 1989;3:219-30.
Strupp et al., Treatment of Cells with Detergent Activates Caspases and Induces Apoptotic Cell Death. J. Membrane Biology. Jun. 2000;175(3): 181-9.
Suresh et al., Bispecific Monoclonal Antibodies from Hybrid Hybridomas. Methods in Enzymology. 1986;121:210-28.
Suzuki et al., Possible Existence of Common Internalization Mechanisms among Arginine-rich Peptides. J. Biol. Chem. 2002;277:2437-43.
Terradillos et al. FEBS Lett. 2002;522(1-3):29-34.
Traunecker et al., Bispecific single chain molecules (Janusins) target cytotoxic lymphocytes on HIV infected cells. EMBO J. 1991;10:3655-9.
Tutt et al., Trispecific F(ab')3 derivatives that use cooperative signaling via the TCR/CD3 complex and CD2 to activate and redirect resting cytotoxic T cells. J. Immunol. 1991;147:60.
Vaux et al., Bcl-2 gene promotes haemopoietic cell survival and cooperates with c-myc to immortalize pre-B cells. Nature. 1988;335(6189):440-42.
Verhoeyen et al., Reshaping Human Antibodies: Grafting an Antilysozyme Activity. Science. 1988;239:1534-6.
Vieira et al., Cell permeable BH3-peptides overcome the cytoprotective effect of Bcl-2 and Bcl-XL. Oncogene. 2002 21:1963-77.
Vitetta et al., Redesigning Nature's Poisons to Create Anti-Tumor Reagents. Science. 1987;238:1098-104.

(56) References Cited

OTHER PUBLICATIONS

Vives et al., A Truncated HIV-1 Tat Protein Basic Domain Rapidly Translocates through the Plasma Membrane and Accumulates in the Cell Nucleus. J. Biol. Chem. 1997;272(25):16010-7.

Vo et al., Relative mitochondrial priming of myeloblasts and normal HSCs determines chemotherapeutic success in AML. Cell. Oct. 12, 2012;151(2):344-55.

Wang et al., Bid: A Novel BH3 Domain-Only Death Agonist. Genes Dev. 1996;10(22):2859-69.

Wang et al., Cell Permeable Bcl-2 binding Peptides: A Chemical Approach to Apoptosis Induction in Tumor Cells. Cancer Res. 2000;60:1498-502.

Wang et al., Structure based discovery of an organic compound that binds Bcl-2 protein and induces apoptosis of tumor cells. PNAS. 2000;97:7124-9.

Wang, The Expanding Role of Mitochondria in Apoptosis. Genes Dev. 2001;15:2922-33.

Wei et al., Proapoptotic BAX and BAK: A Requisite Gateway to Mitochondrial Dysfunction and Death. Science. 2001;292(5517):727-30.

Wei et al., tBID, a membrane-targeted death ligand, oligomerizes BAK to release cytochrome c. Genes & Development. 2000;14:2060-71.

Weinstein, Addiction to Oncogenes—the Achilles Heal of Cancer. Science. 2002;297:63-4.

Werner et al., Bcl-2 Family Member Bfl-1/A1 Sequesters Truncated Bid to Inhibit its Collaboration With Pro-Apoptotic Bak or Bax. J. Biol. Chem. 2002;277(25):22781-8.

Westerhoff et al., Magainins and the disruptioin of membrane-linked free-energy transduction. Proc. Natl. Acad. Sci. USA. Sep. 1989;86(17):6597-601.

Wilkinson, Immunochemical techniques inspire development of new antibody purification methods. The Scientist. 2000;14(8):25-8.

Willis et al., Apoptosis Initiated When BH3 Ligands Engage Multiple Bcl-2Homologs, not Bax or Bak. Science. Feb. 2007;315:856-9.

Willis et al., Proapoptotic Bak is sequestered by Mcl-1 and Bcl-xL, but not Bcl-2, until displaced by BH3-only proteins. Genes Dev. 2005;19:1294-305.

Wolff et al., Monoclonal antibody homodimers: Enhanced antitumor activity in Nude Mice. Cancer Research. 1993;53:2560-5.

Wolter et al., Movement of Bax from the Cytosol to Mitochondria during Apoptosis. J. Cell Biol. 1997;139(5):1281-92.

Yamaguchi et al., Bcl-XL Protects BimEL-induced Bax Conformational Change and Cytochrome c Release Independent of Interacting with Bax or BimEL. J. Biol. Chem. 2002;277(44):41604-12.

Yang et al., Bad, a Heterodimeric Partner for Bcl-$X_L$ and Bcl-2, Displaces Bax and Promotes Cell Death. Cell. 1995;80(2):285-91.

Yang et al., Calculation of Protein Conformation from Circular Dichroism. Methods Enzymol. 1986;130:208-69.

Yasuda et al., BNIP3 α: a Human Homolog of Mitochondrial Proapoptotic protein BNIP3. Cancer Res. 1999;59:533-7.

Yi et al., Inhibition of Bid-induced apoptosis by Bcl-2. tBid insertion, Bax translocation, and Bax/Bak oligomerization suppressed. J Biol Chem. May 9, 2003;278(19):16992-9. Epub Mar. 6, 2003.

Zha et al., BH3 Domain of BAD is Required for Heterodimerization with Bcl-$X_L$ and Pro-apoptotic Activity. J. Biol. Chem. 1997;272(39):24101-4.

Zha et al., Serine Phosphorylation of Death Agonist BAD in Response to Survival Factor Results in Binding to 14-3-3 Not BCL-$X_L$. Cell. 1996;87:619-28.

Zha et al., Posttranslational N-Myristoylation of BID as a Molecular Switch for targeting Mitochondria and Apoptosis. Science. 2000;290(5497)1761-5.

Zhou et al., Novel mutant-selective EGFR kinase inhibitors against EGFR T790M. Nature. Dec. 24, 2009;462(7276):1070-4.

Zong et al., BH3-only proteins that bind pro-survival Bcl-2 family members fail to induce apoptosis in the absence of Bax and Bak. Genes & Development. 2001;15:1481-6.

* cited by examiner

SEQUENCE LISTING

```
<160> NUMBER OF SEQ ID NOS: 15

<210> SEQ ID NO 1
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1

Glu Asp Ile Ile Arg Asn Ile Ala Arg His Leu Ala Gln Val Gly Asp
1               5                   10                  15

Ser Met Asp Arg
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 2

Met Arg Pro Glu Ile Trp Ile Ala Gln Glu Leu Arg Arg Ile Gly Asp
1               5                   10                  15

Glu Phe Asn Ala
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 3

Glu Asp Ile Ile Arg Asn Ile Ala Arg His Ala Ala Gln Val Gly Ala
1               5                   10                  15

Ser Met Asp Arg
            20

<210> SEQ ID NO 4
<211> LENGTH: 25
<212> TYPE: PRT
<213> ORGANISM: Artificial Sequence
```

```
<220> FEATURE:
<223> OTHER INFORMATION: Synthetic Polypeptide

<400> SEQUENCE: 4

Leu Trp Ala Ala Gln Arg Tyr Gly Arg Glu Leu Arg Arg Met Ser Asp
1               5                   10                  15

Glu Phe Glu Gly Ser Phe Lys Gly Leu
            20                  25

<210> SEQ ID NO 5
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 5

Met Glu Gly Ser Asp Ala Leu Ala Leu Arg Leu Ala Cys Ile Gly Asp
1               5                   10                  15

Glu Met Asp Val
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 6

Ala Glu Leu Pro Pro Glu Phe Ala Ala Gln Leu Arg Lys Ile Gly Asp
1               5                   10                  15

Lys Val Tyr Cys
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 7

Pro Ala Asp Leu Lys Asp Glu Cys Ala Gln Leu Arg Arg Ile Gly Asp
1               5                   10                  15

Lys Val Asn Leu
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 8

Ser Ser Ala Ala Gln Leu Thr Ala Ala Arg Leu Lys Ala Leu Gly Asp
1               5                   10                  15

Glu Leu His Gln
            20
```

```
<210> SEQ ID NO 9
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 9

Val Val Glu Gly Glu Lys Glu Val Glu Ala Leu Lys Lys Ser Ala Asp
1               5                   10                  15

Trp Val Ser Asp
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 10

Glu Gln Trp Ala Arg Glu Ile Gly Ala Gln Leu Arg Arg Met Ala Asp
1               5                   10                  15

Asp Leu Asn Ala
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 11

His Gln Ala Glu Val Gln Ile Ala Arg Lys Leu Gln Leu Ile Ala Asp
1               5                   10                  15

Gln Phe His Arg
            20

<210> SEQ ID NO 12
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 12

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 13

Leu Trp Ala Ala Gln Arg Tyr Gly Arg Glu Ala Arg Arg Met Ser Asp
1               5                   10                  15

Glu Phe Glu Gly Ser Phe Lys Gly Leu
            20                  25
```

```
<210> SEQ ID NO 14
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid

<400> SEQUENCE: 14

Xaa Xaa Xaa Xaa Xaa Xaa Ile Ala Xaa Xaa Leu Leu Leu Leu Gly Asp
1               5                   10                  15

Xaa Xaa Xaa Xaa
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid

<400> SEQUENCE: 15

Xaa Xaa Xaa Xaa Xaa Xaa Xaa Xaa Xaa Xaa Leu Xaa Xaa Xaa Xaa Asp
1               5                   10                  15

Xaa Xaa Xaa Xaa
            20
```

METHODS OF BH3 PROFILING

RELATED APPLICATIONS

This application is a national stage filing under 35 U.S.C. § 371 of International Application No. PCT/US2014/056284, filed Sep. 18, 2014, and entitled "METHODS OF BH3 PROFILING," which claims the benefit under 35 U.S.C. § 119(e) of U.S. provisional application Ser. No. 61/879,869, filed Sep. 19, 2013, the contents of which are incorporated by reference herein in their entirety.

FIELD OF THE INVENTION

The invention relates to generally to improved methods of determining cellular chemosensitivity by determining the pattern of sensitively of a cell to a panel of BH3 domain peptides.

BACKGROUND OF THE INVENTION

Programmed cell death, referred to as apoptosis, plays an indispensable role in the development and maintenance of tissue homeostasis within all multicellular organisms (Raff, Nature 356: 397-400, 1992). Genetic and molecular analysis from nematodes to humans has indicated that the apoptotic pathway of cellular suicide is highly conserved (Hengartner and Horvitz, Cell 76: 1107-1114, 1994). In addition to being essential for normal development and maintenance, apoptosis is important in the defense against viral infection and in preventing the emergence of cancer.

Diverse intrinsic death signals emanating from multiple subcellular locales all induce the release of cytochrome c from mitochondria to activate Apaf-1 and result in effector caspase activation. Proteins in the BCL-2 family are major regulators of the commitment to programmed cell death as well as executioners of death signals at the mitochondrion. Members of this family include both pro- and anti-apoptotic proteins and share homology in up to four conserved regions termed BCL-2 homology (BH) 1-4 domains (Adams and Cory, 1998). The family can be divided into three main sub-classes. The anti-apoptotic proteins, which include BCL-2 and BCL-$X_L$, are all "multidomain," sharing homology throughout all four BH domains. However, the pro-apoptotic proteins can be further subdivided and include multidomain proteins, such as BAX and BAK, which possess sequence homology in BH1-3 domains. The more distantly related "BH3-only" proteins are to date all pro-apoptotic and share sequence homology within the amphipathic α-helical BH3 region, which is required for their apoptotic function (Chittenden et al., 1995; O'Connor et al., 1998; Wang et al., 1996; Zha et al., 1997).

Multidomain pro-apoptotic proteins such as BAX and BAK upon receipt of death signals participate in executing mitochondrial dysfunction. In viable cells, these proteins exist as monomers. In response to a variety of death stimuli, however, inactive BAX, which is located in the cytosol or loosely attached to membranes, inserts deeply into the outer mitochondrial membrane as a homo-oligomerized multimer (Eskes et al., 2000; Gross et al., 1998; Wolter et al., 1997). Inactive BAK resides at the mitochondrion where it also undergoes an allosteric conformational change in response to death signals, which includes homo-oligomerization (Griffiths et al., 1999; Wei et al., 2000). Cells deficient in both BAX and BAK are resistant to a wide variety of death stimuli that emanate from multiple locations within the cell (Wei et al., 2001).

The BH3-only molecules constitute the third subset of this family and include BID, NOXA, PUMA, BIK, BIM and BAD (Kelekar and Thompson, 1998). These proteins share sequence homology only in the amphipathic α-helical BH3 region which mutation analysis indicated is required in pro-apoptotic members for their death activity. Moreover, the BH3-only proteins require this domain to demonstrate binding to "multidomain" BCL-2 family members. Multiple binding assays, including yeast two-hybrid, co-immunoprecipitation from detergent solubilized cell lysates and in-vitro pull down experiments indicate that individual BH3-only molecules display some selectivity for multidomain BCL-2 members (Boyd et al., 1995; O'Connor et al., 1998; Oda et al., 2000; Wang et al., 1996; Yang et al., 1995). The BID protein binds pro-apoptotic BAX and BAK as well as anti-apoptotic BCL-2 and BCL-$X_L$ (Wang et al., 1996; Wei et al., 2000). In contrast, BAD, and NOXA as intact molecules display preferential binding to anti-apoptotic members (Boyd et al., 1995; O'Connor et al., 1998; Oda et al., 2000; Yang et al., 1995)

SUMMARY OF THE INVENTION

In various aspects the invention provides methods of predicting sensitivity of a cancer cell to a therapeutic agent by contacting a test cell population with a BH3 domain peptide; measuring the amount of BH3 domain peptide induced mitochondrial outer membrane permeabilization in the test cell population; and comparing the amount of BH3 domain peptide induced mitochondrial outer membrane permeabilization in the test cell population to a control cell population that has not been contacted with the therapeutic agent. An increase in mitochondrial membrane permeabilization in the test cell population compared to the control cell population indicates the cell is sensitive to the therapeutic agent. Optionally, the cell is permeabilized prior to contacting with said BH3 domain peptide.

Mitochondrial outer membrane permeabilization is determined for example by measuring i) the emission of a potentiometric or radiometric dye or ii) the release of molecules from the mitochondrial inter-membrane space.

In some embodiments the permeabilized cells are contacted with a potentiometric dye such as JC-1 or dihydrorhodamine 123. In other embodiments, the permeabilized cell is contacted with an antibody for cytochrome C or SMAC/Diablo, Omi, adenylate kinase-2 or apoptosis inducing factor.

Optionally, the method further includes contacting said permeabilized cell with an antibody for an intracellular or extracellular marker.

In some aspects the cell population is fixed prior to measuring mitochondrial outer membrane permeabilization. For example, the cell population is fixed on a solid surface.

A BH3 domain peptide is derived from the BH3 domain of a BID, a BIM, a BAD, a BIK, a NOXA, a PUMA a BMF, or a HRK polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1A:
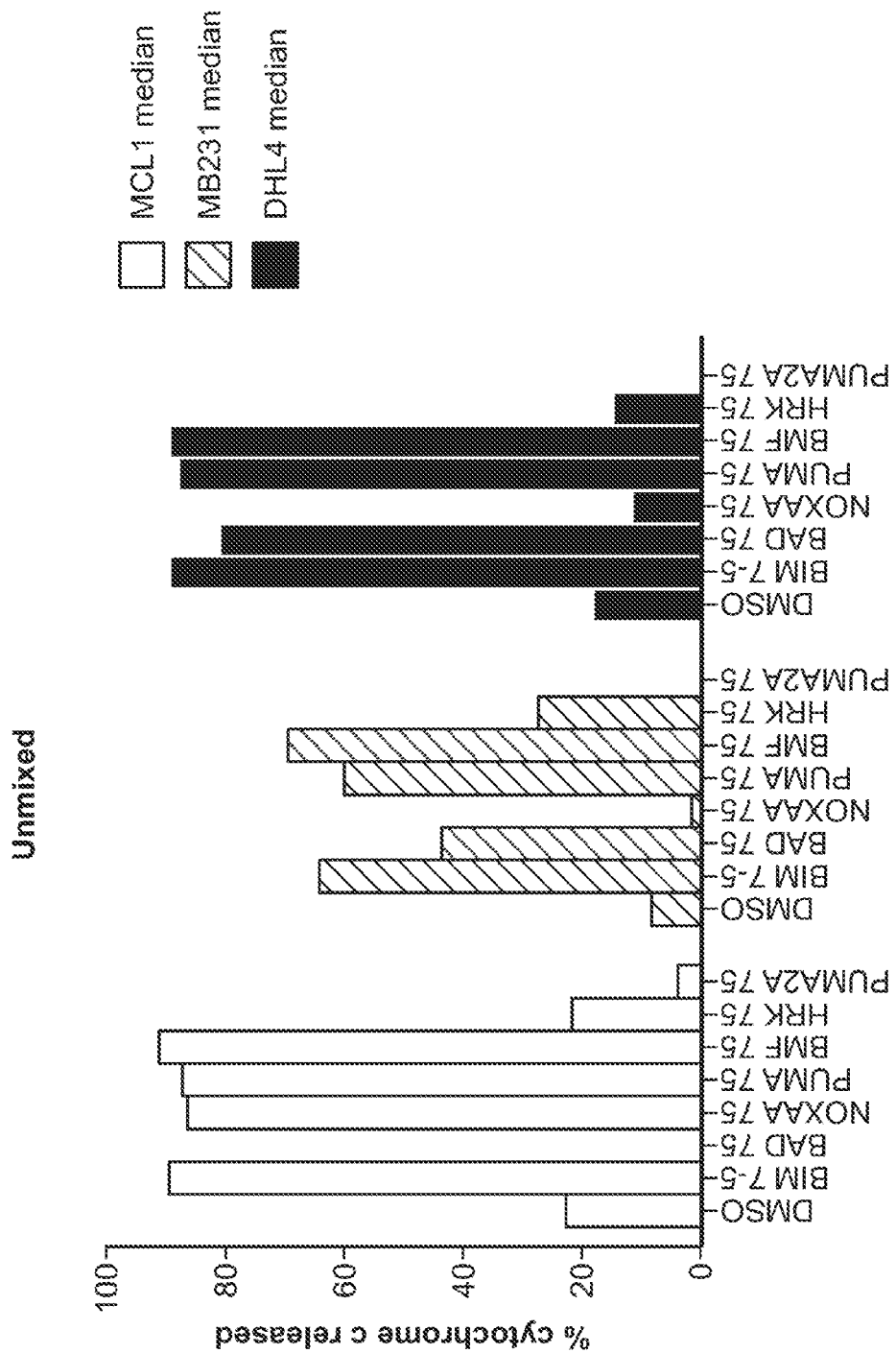
FIG. 1 is a series of bar graphs demonstrating that iBH3 can reproduce the profile of individual subpopulations with mixed populations. Samples profiled individually (unmixed as shown in FIG. 1A) or as a complex mixture (mixed as shown in FIG. 1B) produce the same profile.

The present invention is based in part by the discovery of improved methods of measuring mitochondrial outer membrane permeabilization. These improved methods are useful in BH3 Profiling as described in US2008/0199890, the contents of which are incorporated by reference in its entirety.

BH3 Profiling

In various methods, sensitivity of a cell to an agent is determined. Cell sensitivity is determined by contacting a cell or cellular component (e.g., mitochondria) with a BH3 domain peptide. A cell is sensitive to an agent if apoptosis is detected. Alternatively, cell sensitivity is determined by providing a test BH3 profile of the cell and comparing the profile to a cancer cell BH3 profile. A similarity of the test profile and the control profile indicates that the cell is sensitive to an agent. A BH3 profile is a pattern of sensitivity to BH3 peptides of the cell. Sensitivity is indicated by apoptosis. A cancer cell BH3 profile is a pattern of sensitivity to BH3 peptides in a cancer cell whose responsiveness or lack thereof to a particular agent is known. Optionally, the test BH3 profile is compared to more than one cancer cell BH3 profile. Thus, by comparing the test BH3 profile to the control BH3 profile sensitivity to an agent is determined.

The cell or cellular component is a cancer cell or a cell that is suspected of being cancerous. The cell is permeabilized to permit the BH3 peptides access to the mitochondria. Cells are permeabilized by methods known in the art, for example, the cells are permeabilized by contacting the cell with digitonin.

After the cells are permeabilized the cells are treated with the BH3 peptides or test agents. After the cell is treated, mitochondrial outer membrane permeabilization is measured. Outer membrane permeabilization is measured by a number of methods, for example, outer membrane permeabilization by loss of mitochondrial membrane potential. Loss of mitochondrial membrane potential is measured for example by treating the cells with a potentiometric or radiometric dye.

Alternatively, outer membrane permeabilization is determined by measuring the release of molecules from the mitochondrial inter-membrane space. Examples of molecules that can be measured include cytochrome c and SMAC/Diablo, Omi, adenylate kinase-2 or apoptosis inducing factor (AIF). Optionally, the cells are fixed prior to measuring outer membrane permeabilization. Cells are fixed by methods known in the art such as by using an aldehyde such as formaldehyde.

Mitochondrial outer membrane permeabilization can be measured at the single cell level or multi-cell level or across the entire population of cells. Additionally, some of the methods disclosed herein allow for subpopulations of cells to be assayed.

Examples of potentiometric dyes include green-fluorescent JC-1 probe (5,5',6,6'-tetrachloro-1,1',3,3'-tetraethylbenzimidazolylcarbocyanine iodide) or dihydrorhodamine 123.

JC-1 exists as a monomer at low membrane concentrations). However, JC-1 accumulates in the mitochondrial matrix under conditions of higher mitochondrial potentials. At these higher concentrations, JC-1 forms red-fluorescent "J-aggregates". As a monomer the dye has an absorption/emission maxima of 527 nm while at high membrane potential the emission maximum is 590 nm. Thus, ratio measurements of the emission of this cyanine dye can be used as a sensitive measure of mitochondrial membrane potential. The dye allows for a dual measurement of dye concentration that does not require the measurement of a nuclear or cytoplasmic reference values. Studies using isolated mitochondria have shown that the 527 nm emission from monomeric JC-1 increases almost linearly with membrane M potentials ranging from 46 to 182 mV, whereas the 590 nm J-aggregate emission is less sensitive to M values less negative than 140 my and is strongly sensitive to potential values in the range of 140 to 182 mV (Di Lisa et al., 1995) Optical filters designed for fluorescein and tetramethylrhodamine can be used to separately visualize the monomer and J-aggregate forms, respectively. Alternatively, both forms can be observed simultaneously using a standard fluorescein long pass optical filter set.

Dihydrorhodamine 123 is an uncharged, nonfluorescent agent that can be converted by oxidation to the fluorescent laser dye rhodamine 123 (R123).

Release of molecules from the mitochondrial inter-membrane space can be measured by methods known in the art, for example, by using antibodies to the molecules to be measured, i.e., antibodies to cytochrome C or SMAC/Diablo. Detection can be for example, by ELISA, FACS, immunoblot, immunofluorescence, or immunohistochemistry.

In addition to measuring molecules that get released from the mitochondrial space, other intracellular and extracellular markers can be measured. This allows for the ability to discriminate between subpopulations of cells.

BH3 profiling can be accomplished at the single cell level by immobilizing cells on a solid surface. Optionally the solid surface is polyamine or poly-lysine coated. Immobilized cells are permeabilized as described above. The cells are then contacted with BH3 peptides and/or test agents. After the cells have been treated for a predetermined period of time such as 45-90 minutes, the cells are fixed and further permeabilized by methods known in the art. For example the cells are fixed with formaldehyde and further permeabilized with methanol or Triton X-100 (t-Octylphenoxypolyethoxyethanol). Outer membrane permeabilization is determined by intracellular staining for molecules from the mitochondrial inter-membrane space and a mitochondrial marker. Examples of molecules that can be measured include cytochrome c, SMAC/Diablo, Omi, adenylate kinase-2 or apoptosis inducing factor (AIF). A mitochondrial marker includes MnSOD. Stained cells can be counterstained with nuclear stains such as DAPI. Optionally other intracellular and extracellular markers can be measured. Analysis of the cells can be manually accomplished using a microscope or automated for example by using software such as Cellprofiler to locate nuclei. The cell is from a subject known to or suspected of having cancer. The subject is preferably a mammal. The mammal is, e.g., a human, non-human primate, mouse, rat, dog, cat, horse, or cow. The subject has been previously diagnosed as having cancer, and possibly has already undergone treatment for cancer. Alternatively, the subject has not been previously diagnosed as having cancer.

The agent is a therapeutic agent such as a chemotherapeutic agent. For example the agent is a mimetic of sensitizer BH3 domains or an antagonist of an anti-apoptotic protein. Apoptosis, i.e., cell death is identified by known methods. For example, characteristics of apoptosis include the cell shrinks, develop bubble-like blebs on their surface, have the chromatin (DNA and protein) in their nucleus degraded, and have their mitochondria break down with the release of cytochrome c, loss of mitochondrial membrane potential, break into small, membrane-wrapped, fragments, or phosphatidylserine, which is normally hidden within the plasma membrane, is exposed on the surface of the cell.

The difference in the level apoptosis of a cell that has been contacted with a BH3 peptide compared to a cell that has not been contacted with a BH3 peptide is statistically significant. By statistically significant, it is meant that the alteration is greater than what might be expected to happen by chance alone. Statistical significance is determined by method known in the art. For example statistical significance is determined by p-value. The p-value is a measure of probability that a difference between groups during an experiment happened by chance. ($P(z \geq z_{observed})$). For example, a p-value of 0.01 means that there is a 1 in 100 chance the result occurred by chance. The lower the p-value, the more likely it is that the difference between groups was caused by treatment. An alteration is statistically significant if the p-value is or less than 0.05. Preferably, the p-value is 0.04, 0.03, 0.02, 0.01, 0.005, 0.001 or less.

The invention also includes a profile of a pattern of mitochondrial sensitivity to BH3 sensitizer peptides taken from one or more subjects who have cancer.

BH3 Domain Peptides

A BH3 domain peptide is less than 195 amino acids in length, e.g., less than or equal to 150, 100, 75, 50, 35, 25 or 15 amino acids in length. For example a BH3 peptide includes the sequence of SEQ ID NO: 1-13 shown in Table 1.

TABLE 1

|         | AMINO ACID SEQUENCE         | SEQ ID NO |
|---------|-----------------------------|-----------|
| BID     | EDIIRNIARHLAQVGDSMDR        | 1         |
| BIM     | MRPEIWIAQELRRIGDEFNA        | 2         |
| BID mut | EDIIRNIARHAAQVGASMDR        | 3         |
| BAD     | LWAAQRYGRELRRMSDEFEGSFKGL   | 4         |
| BIK     | MEGSDALALRLACIGDEMDV        | 5         |
| NOXA A  | AELPPEFAAQLRKIGDKVYC        | 6         |
| NOXA B  | PADLKDECAQLRRIGDKVNL        | 7         |
| HRK     | SSAAQLTAARLKALGDELHQ        | 8         |
| BNIP    | VVEGEKEVEALKKSADWVSD        | 9         |
| PUMA    | EQWAREIGAQLRRMADDLNA        | 10        |
| BMF     | HQAEVQIARKLQLIADQFHR        | 11        |
| huBAD   | NLWAAQRYGRELRRMSDEFVDSFKK   | 12        |
| BAD mut | LWAAQRYGREARRMSDEFEGSFKGL   | 13        |

A BH3 domain peptide include a peptide which includes (in whole or in part) the sequence NH$_2$-XXXXXXIAXX-LXXXGDXXXX-COOH (SEQ ID NO:14) or NH$_2$-XXXXXXXXXXLXXXXDXXXX-COOH (SEQ ID NO:15). As used herein X may be any amino acid. Alternatively, the BH3 domain peptides include at least 5, 6, 7, 8, 9, 15 or more amino acids of SEQ ID NO:14 or SEQ ID NO:15.

Optionally, the BH3 domain peptide is attached to transduction domain. A transduction domain is a compound that directs a peptide in which it is present to a desired cellular destination. Thus, the transduction domain can direct the peptide across the plasma membrane, e.g., from outside the cell, through the plasma membrane, and into the cytoplasm. Alternatively, or in addition, the transduction domain can direct the peptide to a desired location within the cell, e.g., the nucleus, the ribosome, the ER, mitochondria, a lysosome, or peroxisome.

In some embodiments, the transduction domain is derived from a known membrane-translocating sequence. Alternatively, the transduction domain is a compound that is known to facilitate membrane uptake such as polyethylene glycol, cholesterol moieties, octanoic acid and decanoic acid.

For example, the trafficking peptide may include sequences from the human immunodeficiency virus (HIV) 1 TAT protein. This protein is described in, e.g., U.S. Pat. Nos. 5,804,604 and 5,674,980, each incorporated herein by reference. The BH3 domain peptide is linked to some or all of the entire 86 amino acids that make up the TAT protein. For example, a functionally effective fragment or portion of a TAT protein that has fewer than 86 amino acids, which exhibits uptake into cells can be used. See e.g., Vives et al., *J. Biol. Chem.*, 272(25):16010-17 (1997), incorporated herein by reference in its entirety. A TAT peptide that includes the region that mediates entry and uptake into cells can be further defined using known techniques. See, e.g., Franked et al., *Proc. Natl. Acad. Sci, USA* 86: 7397-7401 (1989). Other sources for translocating sequences include, e.g., VP22 (described in, e.g., WO 97/05265; Elliott and O'Hare, Cell 88: 223-233 (1997)), *Drosophila* Antennapedia (Antp) homeotic transcription factor, HSV, poly-arginine, poly lysine, or non-viral proteins (Jackson et al, *Proc. Natl. Acad. Sci. USA* 89: 10691-10695 (1992)).

The transduction domain may be linked either to the N-terminal or the C-terminal end of BH3 domain peptide. A hinge of two proline residues may be added between the transduction domain and BH3 domain peptide to create the full fusion peptide. Optionally, the transduction domain is linked to the BH3 domain peptide in such a way that the transduction domain is released from the BH3 domain peptide upon entry into the cell or cellular component.

The transduction domain can be a single (i.e., continuous) amino acid sequence present in the translocating protein. Alternatively it can be two or more amino acid sequences, which are present in protein, but in the naturally-occurring protein are separated by other amino acid sequences.

The amino acid sequence of naturally-occurring translocation protein can be modified, for example, by addition, deletion and/or substitution of at least one amino acid present in the naturally-occurring protein, to produce modified protein. Modified translocation proteins with increased or decreased stability can be produced using known techniques. In some embodiments translocation proteins or peptides include amino acid sequences that are substantially similar, although not identical, to that of naturally-occurring protein or portions thereof. In addition, cholesterol or other lipid derivatives can be added to translocation protein to produce a modified protein having increased membrane solubility.

The BH3 domain peptide and the transduction domain can be linked by chemical coupling in any suitable manner known in the art. Many known chemical cross-linking methods are non-specific, i.e.; they do not direct the point of coupling to any particular site on the transport polypeptide or cargo macromolecule. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, CHEMICAL MODIFICATION OF PROTEINS, Holden-Day, 1974, pp. 39-43. Among these reagents are, for example, J-succinimidyl 3-(2-pyridyldithio) propionate (SPDP) or N, N'-(1,3-phenylene) bismaleimide (both of which are highly specific for sulfhydryl groups and form irreversible linkages); N, N'-ethylene-bis-(iodoacetamide) or other such reagent having 6 to 11 carbon methylene bridges (which relatively specific for sulfhydryl groups); and 1,5-difluoro-2, 4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl) cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651 H).

The BH3 domain peptides and/or the transduction domain peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., *Nature,* 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Alternatively, the BH3 domain peptides and/or the transduction domain peptides are cyclic peptides. Cyclic peptides are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology,* 137: 5182-5185 (1996)), or between two amino acid side chains. See, e.g., DeGrado, *Adv Protein Chem,* 39: 51-124 (1988).

BH3 domain peptides and/or the transduction domain peptides are easily prepared using modern cloning techniques, or may be synthesized by solid state methods or by site-directed mutagenesis. A BH3 domain peptide and/or the transduction domain peptides may include dominant negative forms of a polypeptide. In one embodiment, native BH3 domain peptides and/or transduction domain peptides can be isolated from cells or tissue sources by an appropriate purification scheme using standard protein purification techniques. In another embodiment, BH3 domain polypeptides and/or transduction domain peptides are produced by recombinant DNA techniques. Alternative to recombinant expression, BH3 domain peptides and/or transduction domain peptides can be synthesized chemically using standard peptide synthesis techniques.

In various embodiments, the BH3 peptide maintains its secondary structure, e.g. α-helical structure. Methods of helix stabilization are known in the art.

Preferably, the BH3 peptide is a stable peptide. By "stable "it is meant that the peptide possess stability sufficient to allow the manufacture and which maintains the integrity of the compound for a sufficient period of time to be useful for the purposes detailed herein. For example the peptides are covalently stabilized using polar and or labile crosslinks (Phelan et al. 1997 J. Am. Chem. Soc. 119:455; Leuc et al. 2003 Proc. Nat'l. Acad. Sci. USA 100:11273; Bracken et al., 1994 J. Am. Chem. Soc. 116:6432; Yan et al. 2004 Bioorg. Med. Chem. 14:1403). Alternatively, the peptides are stabilized using the metathesis-based approach, which employed .alpha., .alpha.-disubstituted non-natural amino acids containing alkyl tethers (Schafmeister et al., 2000 J. Am. Chem. Soc. 122:5891; Blackwell et al. 1994 Angew Chem. Int. Ed. 37:3281). Preferably the peptides are stabilized using hydrocarbon stapling. Stapled peptides are chemically braced or "stapled" peptides so that their shape, and therefore their activity, is restored and/or maintained. Stably cross-linking a polypeptide having at least two modified amino acids (a process termed "hydrocarbon stapling") can help to conformationally bestow the native secondary structure of that polypeptide. For example, cross-linking a polypeptide predisposed to have an alpha-helical secondary structure can constrain the polypeptide to its native alpha-helical conformation. The constrained secondary structure can increase resistance of the polypeptide to proteolytic cleavage and also increase hydrophobicity. Stapled BH3 peptides are produced for example, as described in WO05044839A2, herein incorporate by reference in its entirety. Alternatively, the BH3 peptides are cyclic peptides. Cyclic peptides are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology,* 137: 5182-5185 (1996)), or between two amino acid side chains. See, e.g., DeGrado, *Adv Protein Chem,* 39: 51-124 (1988).

An "isolated" or "purified" protein or biologically active portion thereof is substantially free of cellular material or other contaminating proteins from the cell or tissue source from which the BH3 domain peptide is derived, or substantially free from chemical precursors or other chemicals when chemically synthesized. The language "substantially free of cellular material" includes preparations of BH3 peptides and/or transduction domain peptides in which the protein is separated from cellular components of the cells from which it is isolated or recombinantly produced. In one embodiment, the language "substantially free of cellular material" includes preparations of BH3 domain peptides and/or the transduction domain peptides having less than about 30% (by dry weight) of non-BH3 domain peptide and/or non-transduction domain peptides (also referred to herein as a "contaminating protein"), more preferably less than about 20% of non-BH3 peptide and/or non-transduction domain peptides, still more preferably less than about 10% of non-BH3 peptide and/or non-transduction domain peptides, and most preferably less than about 5% non-BH3 domain peptide and/or non-transduction domain peptides. When the BH3 domain peptide and/or the transduction domain peptides or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of BH3 domain peptides and/or the transduction domain peptides in which the protein is separated from chemical precursors or other chemicals that are involved in the synthesis of the protein. In one embodiment, the language "substantially free of chemical precursors or other chemicals" includes preparations of BH3 domain peptides and/or transduction domain peptides having less than about 30% (by dry weight) of chemical precursors or non-BH3 domain peptide and/or non-transduction domain peptides chemicals, more preferably less than about 20% chemical precursors or non-BH3 domain peptide and/or non-transduction domain peptides chemicals, still more preferably less than about 10% chemical precursors or non-BH3 domain peptide chemicals, and most preferably less than about 5% chemical precursors or non-BH3 domain peptide and/or non-transduction domain peptides chemicals.

The term "biologically equivalent" is intended to mean that the compositions of the present invention are capable of demonstrating some or all of the same apoptosis modulating effects, i.e., release of cytochrome C or BAK oligomerization although not necessarily to the same degree as the BH3 domain polypeptide deduced from sequences identified from cDNA libraries of human, rat or mouse origin or produced from recombinant expression symptoms.

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to sequences as indicated above for identity comparisons. Conservative amino acid changes satisfying this requirement are: R-K; E-D, Y-F, L-M; V-I, Q-H.

BH3 domain peptides can also include derivatives of BH3 domain peptides which are intended to include hybrid and modified forms of BH3 domain peptides including fusion proteins and BH3 domain peptide fragments and hybrid and modified forms in which certain amino acids have been deleted or replaced and modifications such as where one or more amino acids have been changed to a modified amino acid or unusual amino acid and modifications such as glycosylation so long as the hybrid or modified form retains the biological activity of BH3 domain peptides. By retaining the biological activity, it is meant that cell death is induced by the BH3 polypeptide, although not necessarily at the same level of potency as that of the naturally-occurring BH3 domain polypeptide identified for human or mouse and that can be produced, for example, recombinantly. The terms induced and stimulated are used interchangeably throughout the specification.

Preferred variants are those that have conservative amino acid substitutions made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BH3 domain polypeptide is replaced with another amino acid residue from the same side chain family. Alternatively, in another embodiment, mutations can be introduced randomly along all or part of a BH3 coding sequence, such as by saturation mutagenesis, and the resultant mutants can be screened to identify mutants that retain activity.

Also included within the meaning of substantially homologous is any BH3 domain peptide which may be isolated by virtue of cross-reactivity with antibodies to the BH3 domain peptide described herein or whose encoding nucleotide sequences including genomic DNA, mRNA or cDNA may be isolated through hybridization with the complementary sequence of genomic or subgenomic nucleotide sequences or cDNA of the BH3 domain peptides herein or fragments thereof.

Also included in the invention are kits for performing BH3 Profiling using whole cells. The kit consists of a multi-well plate containing staining components in a mitochondrial buffer and a tube of mitochondrial buffer for the suspension and dispensing of cells into the plate for analysis. Each well of the multi-well plate contains a mixture of JC-1 dye, oligomycin, 2-mercaptoethanol, digitonin, and a peptide or small molecule at twice their final concentration, Optionally the plate and suspension buffer tube can be frozen for later use along with the suspension buffer tube. To use, the plate and buffer tube are thawed and brought to room temperature. Cells are suspended in buffer, dispensed into the wells of the plate, and analyzed in a fluorescence plate reader using the JC-1 red fluorescence at 590 nm with excitation at 545 nm.

The invention will be further illustrated in the following non-limiting examples.

EXAMPLES

Figure 1B:
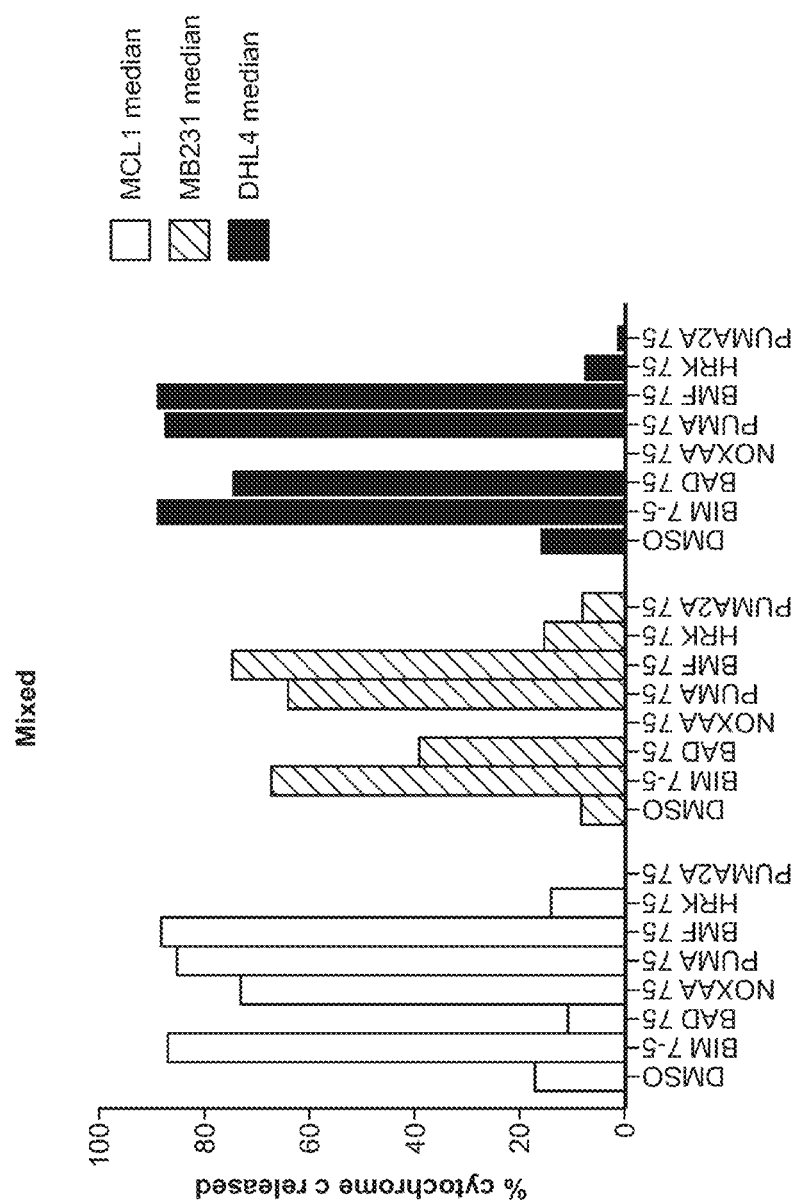
Figure 2A:
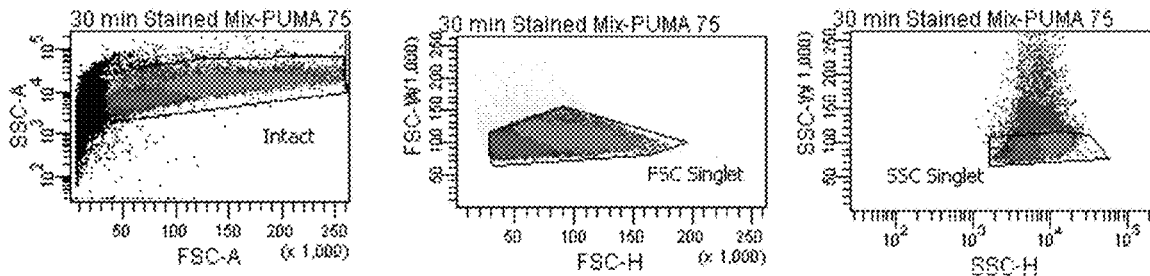
FIG. 2 is a series of panels showing how iBH3 defines cell populations and measures cellular response to profiling. Representative FACS data (FIG. 2A and FIG. 2B) demonstrate the isolation of subpopulations within the mixed sample in FIG. 1.
Figure 2B:
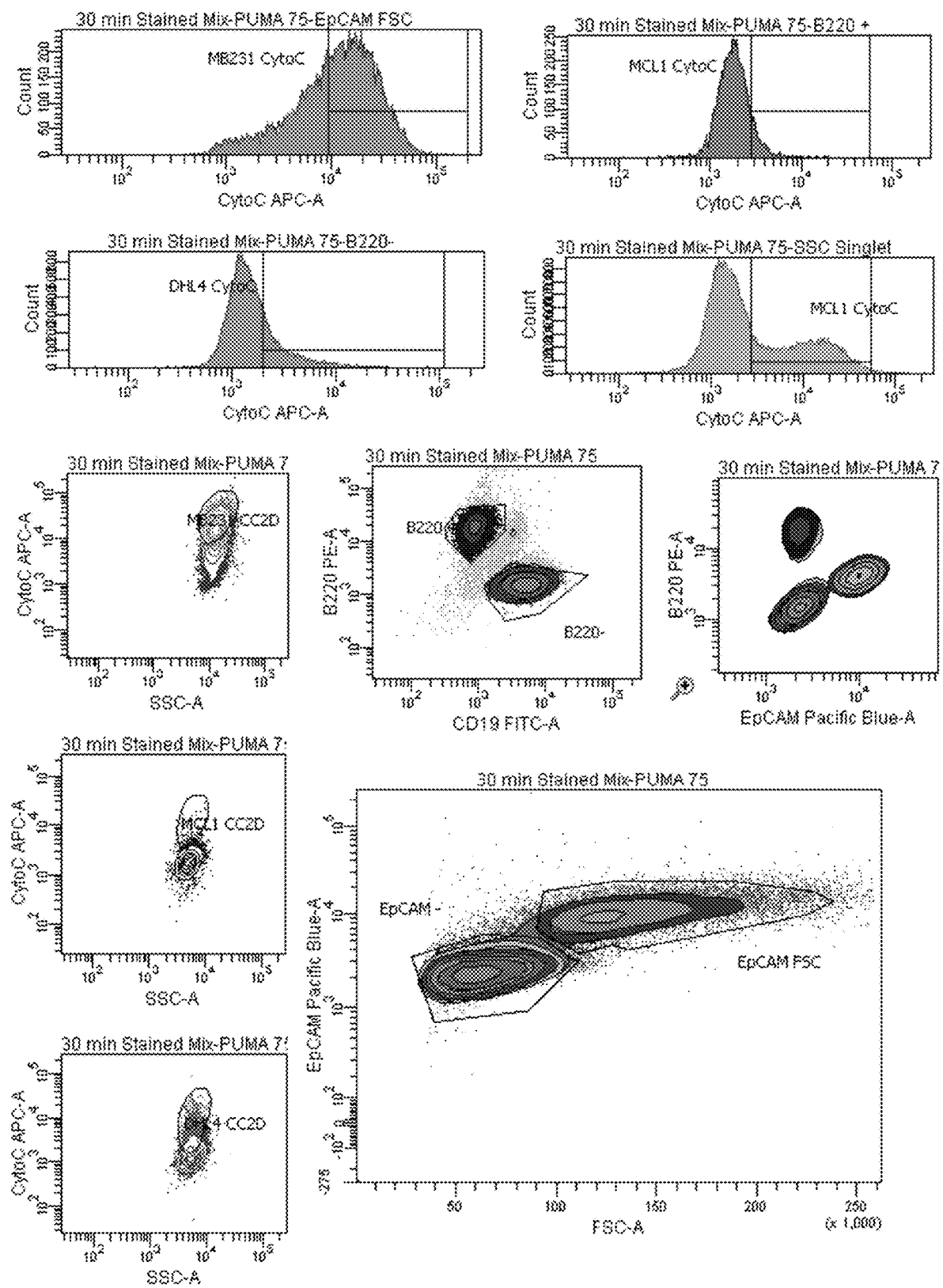
Figure 3:
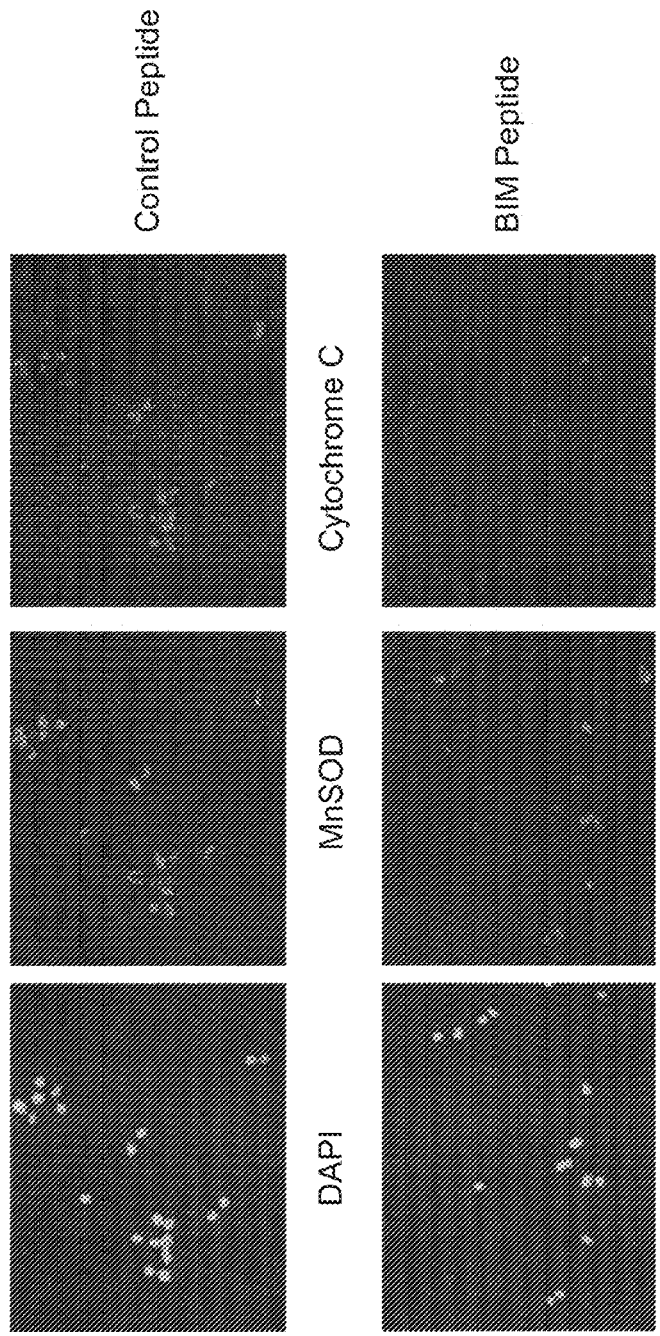
FIG. 3 is a series of fluorescent microscopy images that show the loss of cytochrome c in response to peptide treatment measured by microscopy. Cells are located by DAPI staining of their nuclei, mitochondria are located by staining of a mitochondrial marker (MnSOD) adjacent to nuclei, and cytochrome c staining is correlated with regions of mitochondrial marker staining. An inert control peptide shows cytochrome c staining in regions of MnSOD staining while BIM peptide causes almost total loss of cytochrome c from all regions of MnSOD staining.
Figure 4A:
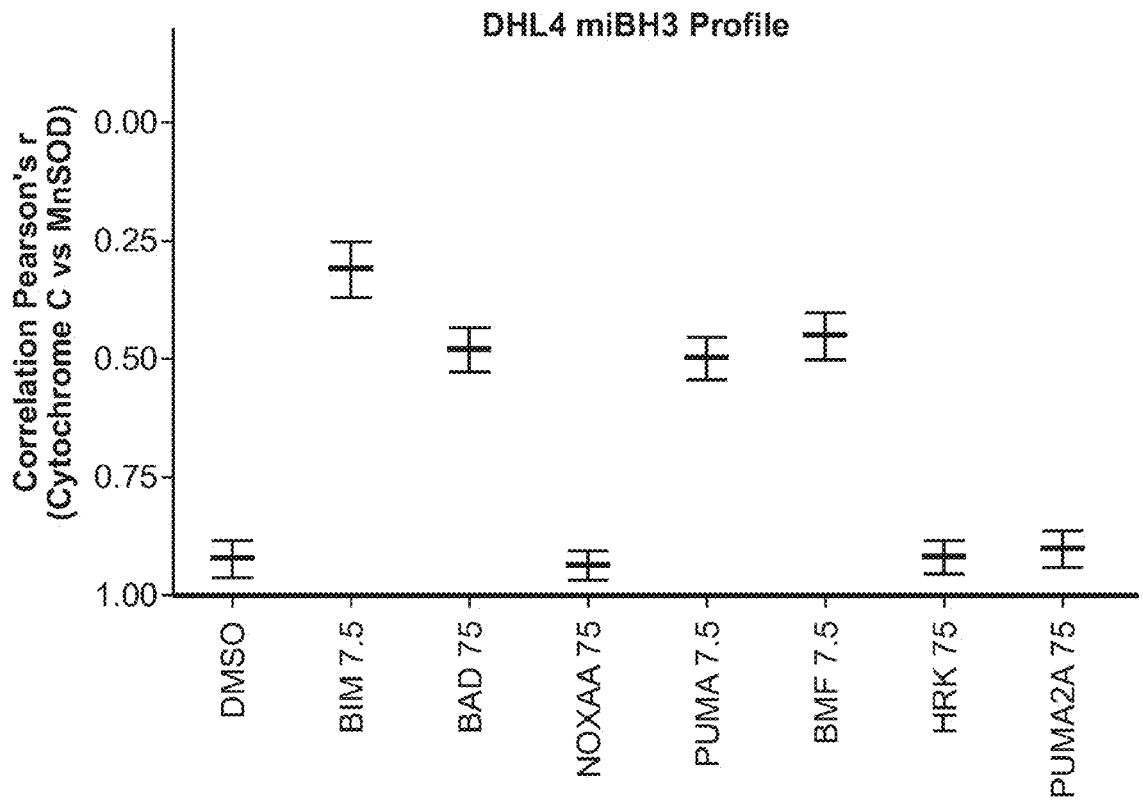
FIG. 4 is a series of bar graphs showing correlation of miBH3 profiles with known profiles. The miBH3 profile of the SuDHL4 cell line (FIG. 4A) shows loss of correlation between cytochrome c and MnSOD channels in response to BH3 peptides. Release of cytochrome c and loss of correlation for BIM, BAD, PUMA, and BMF peptides match the loss of cytochrome c measured by other BH3 profiling methods shown in FIG. 4B.
Figure 4B:
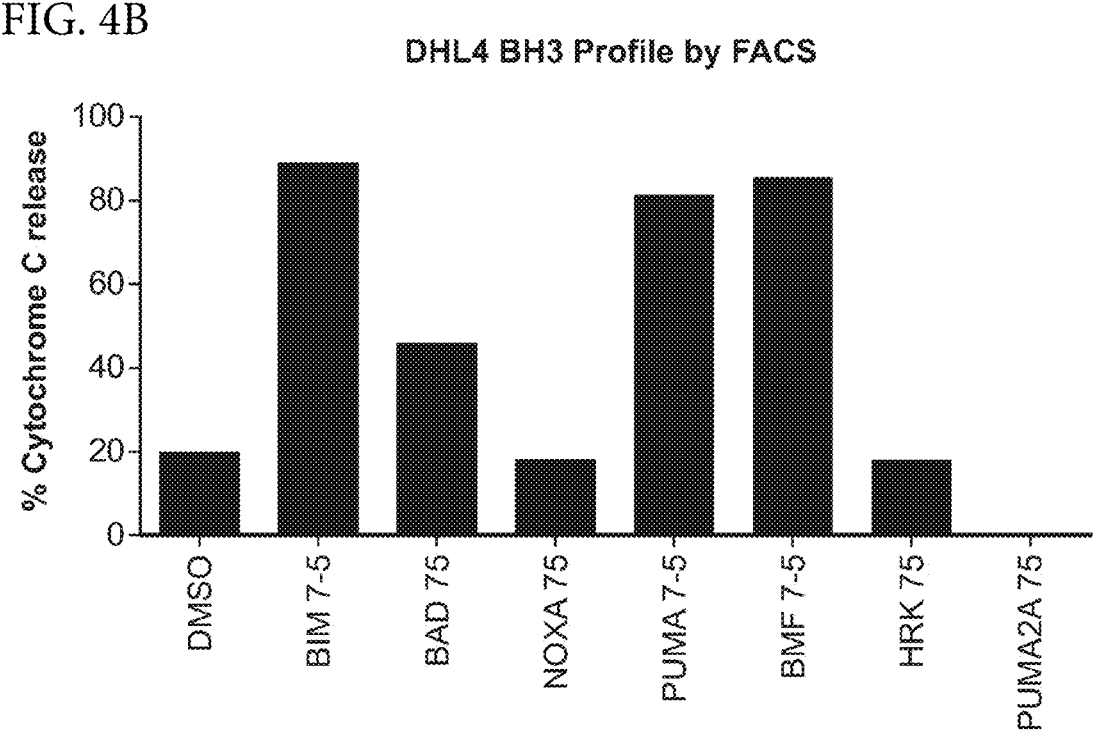
Figure 5:
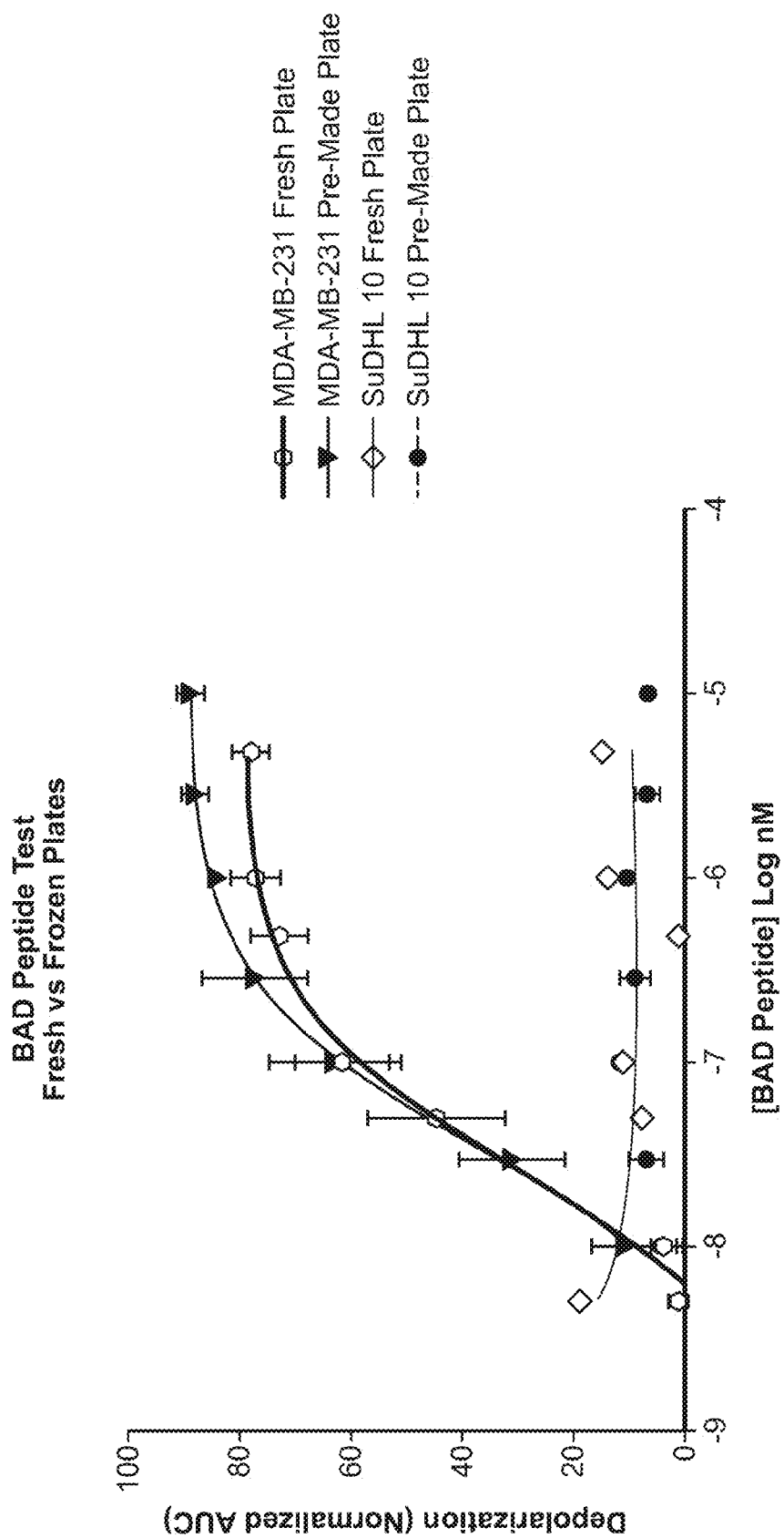
FIG. 5 is a graph showing that pre-made frozen plates perform the same as freshly prepared plates. Responsive cells (MDA-MB-231) show comparable response to a peptide treatment (BAD) in both frozen and freshly prepared plates. Non-responsive cells (SuDHL10) are used to test for non-specific noise, and frozen plates produce a response equivalent to freshly prepared plates.

Example 1: IBH3: BH3 Profiling by Direct Measurement of Retained Cytochrome C by FACS iBH3 adds a key fixation step to prior protocols for BH3 profiling. This produced a better signal, increased sample stability, and improved staining to discriminate subsets in complex clinical samples. Primary tissue or cell cultures are dissociated into single cell suspensions, optionally stained for cell surface markers, and suspended in DTEB Mitochondria] buffer (BH3 profiling in whole cells by fluorimeter or FACS. Methods. 2013 Apr. 20. Epub ahead of print). The suspended cells are then added to wells containing DTEB supplemented with digitonin (a permeabilizing agent) and either peptides or small molecules, which can be prepared and frozen in sample tubes or plates, to allow the molecules or peptides to access the mitochondria and allow for the free diffusion of cytochrome c out of permeabilized mitochondria and out of the cell. Cells are exposed to peptides/small molecules for period of time before a short aldehyde fixation followed by neutralization with a Tris/Glycine buffer. Anti-cytochrome c antibody is then added to each well as a concentrate with saponin, fetal bovine serum, and bovine serum albumin to stain cytochrome c retained by the cells. Other antibodies to intracellular targets can be added at this time. Cells are analyzed by FACS to provide single cell measurements of cytochrome c after perturbation with peptides or small molecules to provide diagnostic response signatures. (FIG. 1: iBH3 faithfully reproduces the profile of individual subpopulations within mixed populations. Samples profiled individually (unmixed) or as a complex mixture (mixed) produce the same profile. This ability to discriminate subpopulations can be applied to any antigen or signal whether intra or extracellular.

This is an improvement over ELISA based BH3 profiling because it can analyze subpopulations within samples, and it is the only method capable of profiling using both extracellular and intracellular markers. Furthermore, it is capable of performing this analysis in high throughput format and can be used with pre-made frozen test plates without the time sensitivity of live mitochondrial potential measurements using potentiometric dyes.

Example 2: MicroBH3: Single Cell BH3 Profiling by Immunofluorescence Microscopy

MicroBH3 (miBH3) is a BH3 profiling method where the measurement of the mitochondrial effect of 9H3 peptides have on individual cells by microscopy. To accomplish this, cells are immobilized on polyamine or poly-lysine coated surfaces and treated with low concentrations of digitonin in a mitochondrial buffer to permeabilize the plasma membrane and grant access to the mitochondria without cell disruption. Fixed concentrations of BH3 peptides or chemical compounds are added for a fixed time, generally 45-90 min, before formaldehyde fixation and permeabilization by methanol and/or Triton X-100 (t-Octylphenoxypolyethoxyethanol) for intracellular staining of cytochrome C and a mitochondrial marker such as MnSOD. Stained cells are counterstained with nuclear stains such as DAPI, and fluorescent images are acquired in nuclear, mitochondrial, and cytochrome c channels. Automated analysis is performed using software such as Cellprofiler to locate nuclei, define regions adjacent to nuclei that have mitochondria, and then correlate the presence of cytochrome c with the location of the mitochondria. Loss of localization indicates a loss of cytochrome c and a reaction to the peptide or compound. This method allows the response of cells to BH3 peptides or compounds and determine their apoptotic propensity, or priming, at a single cell level. Previous methods of analyzing mitochondrial integrity using potential sensitive fluorescent dyes use intact, not permeabilized, cells and cannot be used with BH3 peptides as they are not cell permeant. Permeabilized cells treated with potential sensitive change shape and are difficult to keep in focus for the necessary time courses and are sensitive to timing. Fixed cells by this method can be readily stopped at the fixation step and can be analyzed weeks after acquisition as well as readily re-analyzed if needed.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of predicting sensitivity of a cancer cell population to a cytotoxic agent, the method comprising:
   a) providing a single cell suspension of cells from a cancer cell population;
   b) permeabilizing the cells in the single cell suspension to provide in the single cell suspension permeabilized cells containing intact mitochondria;
   c) contacting the permeabilized cells with a BH3 domain peptide;
   d) fixing the permeabilized cells with a fixative;
   e) staining the fixed permeabilized cells for a molecule from the mitochondrial intermembrane space; and
   f) detecting the staining for the molecule from the mitochondrial intermembrane space to determine an amount of the molecule retained by the permeabilized cells, wherein a decrease in the amount of the molecule retained by the permeabilized cells in the presence of the BH3 domain peptide compared to an amount of the molecule retained by permeabilized cells not contacted with the BH3 domain peptide indicates that the cancer cell population is sensitive to the cytotoxic agent.

2. The method of claim 1, wherein the fixative is an aldehyde.

3. The method of claim 1, wherein the fixed cells are stored prior to detecting the staining.

4. The method of claim 3, wherein the fixed cells are stored for one or more weeks after the fixing.

5. The method of claim 1, wherein the molecule from the mitochondrial intermembrane space is cytochrome c, SMAC/Diablo, Omi, adenylate kinase 2, or apoptosis-inducing factor.

6. The method of claim 1, wherein the staining for the molecule from the mitochondrial intermembrane space is measured by fluorescence-activated cell sorting (FACS).

7. The method of claim 1, wherein the cells are permeabilized with digitonin, methanol, or p-Octylphenoxypolyethoxyethanol.

8. The method of claim 1, wherein the BH3 domain peptide is derived from the BH3 domain of a BH3-interacting domain death agonist (BID), a Bcl-2-interacting mediator of cell death (BIM), a Bcl-2-associated death promoter (BAD), a Bcl-2-interacting killer (BIK), a Noxa, a p53 up-regulated modulator of apoptosis (PUMA), a Bcl-2-modifying factor (BMF), or a harakiri (HRK) polypeptide.

9. The method of claim 1, wherein the BH3 domain peptide includes a sequence selected from the group consisting of SEQ ID NOs. 1, 2, 3, 4, 5, 6, 7, 8, 9, 10, 11, 12, and 13.

10. The method of claim 1, further comprising obtaining the single cell suspension of cells from a tissue sample or cell culture.

11. The method of claim 1, further comprising staining the cells for a cell surface marker, an intracellular marker, or a combination thereof to permit discrimination between cell subpopulations in the cells based on expression of the cell surface marker, the intracellular marker, or combination thereof.

12. The method of claim 11, further comprising detecting the staining of the cell surface marker, the intracellular marker, or the combination thereof, by FACS.

13. The method of claim 1, wherein the permeabilized cells are contacted with the BH3 domain peptide for between about 45 minutes and about 90 minutes.

14. A method of predicting sensitivity of a cancer cell to a cytotoxic agent, the method comprising:
a) immobilizing the cancer cell on a solid surface;
b) permeabilizing the cancer cell to provide a permeabilized cell containing intact mitochondria;
c) contacting the permeabilized cell with a BH3 domain peptide;
d) fixing the permeabilized cell with a fixative;
e) staining the fixed permeabilized cell for a molecule from the mitochondrial intermembrane space and staining the fixed permeabilized cell for an intracellular marker; and
f) detecting the staining by microscopy to locate the molecule from the mitochondrial intermembrane space relative to the intracellular marker in the cancer cell,
wherein loss of localization of the molecule from the mitochondrial intermembrane space in the cancer cell indicates that the cancer cell is sensitive to the cytotoxic agent.

15. The method of claim 14, further comprising wherein staining the fixed permeabilized cell for the intracellular marker comprises staining for one or both of a mitochondrial marker or a nuclear marker.

16. The method of claim 15, wherein the fixed permeabilized cell is stained with DAPI (4',6-diamidino-2-phenylindole).

17. The method of claim 15, wherein the mitochondrial marker is MnSOD.

18. The method of claim 14, wherein the solid surface comprises a polyamine-coated surface or a polylysine-coated surface.

19. The method of claim 14, wherein the molecule from the mitochondrial intermembrane space is cytochrome c.

20. The method of claim 14, wherein the permeabilized cells are contacted with the BH3 domain peptide for between about 45 minutes and about 90 minutes.

* * * * *

UNITED STATES PATENT AND TRADEMARK OFFICE
CERTIFICATE OF CORRECTION

PATENT NO. : 10,739,333 B2
APPLICATION NO. : 15/022987
DATED : August 11, 2020
INVENTOR(S) : Jeremy Ryan et al.

Page 1 of 1

It is certified that error appears in the above-identified patent and that said Letters Patent is hereby corrected as shown below:

In the Claims

In Claim 15, at Column 22, Lines 15-18, the text: "The method of claim 14, further comprising wherein staining the fixed permeabilized cell for the intracellular marker comprises staining for one or both of a mitochondrial marker or a nuclear marker." should be replaced with: -- The method of claim 14, wherein staining the fixed permeabilized cell for the intracellular marker comprises staining for one or both of a mitochondrial marker or a nuclear marker. --.

Signed and Sealed this
Fifteenth Day of December, 2020

Andrei Iancu
*Director of the United States Patent and Trademark Office*